(12) United States Patent
Davis et al.

(10) Patent No.: US 6,319,919 B1
(45) Date of Patent: *Nov. 20, 2001

(54) GALANTHAMINE DERIVATIVES FOR TREATMENT OF ALZHEIMER'S DISEASE

(75) Inventors: Bonnie Davis, 17 Seacrest Dr., Huntington, NY (US) 11743; Madeleine M. Joullie, Philadelphia, PA (US)

(73) Assignee: Bonnie Davis, Syosset, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 08/476,383

(22) Filed: Jun. 7, 1995

Related U.S. Application Data

(63) Continuation of application No. 08/139,338, filed on Oct. 19, 1993, which is a continuation of application No. 07/781,028, filed on Oct. 18, 1991, now abandoned, which is a continuation-in-part of application No. 07/695,949, filed on May 6, 1991, now abandoned, and a continuation of application No. 07/046,522, filed on May 4, 1987, now abandoned, said application No. 07/695,949, is a continuation of application No.07/541,076, filed on Jun. 21, 1990, which is a continuation of application No. 07/219,914, filed on Jul. 15, 1988, now abandoned, which is a continuation-in-part of application No. 07/046,522.

(30) Foreign Application Priority Data

Jan. 15, 1987 (EP) .................................................. 87100461

(51) Int. Cl.$^7$ ..................... C07D 491/06; C07D 487/06; A61K 31/553; A61K 31/55
(52) U.S. Cl. ........................... 514/215; 540/557; 540/581
(58) Field of Search .................... 540/556, 581; 514/215

(56) References Cited

U.S. PATENT DOCUMENTS 3,673,177  6/1972  Morlock .......................... 260/240.3

FOREIGN PATENT DOCUMENTS

| 236684 | * | 9/1987 | (EP) . |
| 2039892 | | 8/1980 | (GB) . |
| 2039892 | | 10/1980 | (GB) . |
| 4713919 | | 4/1972 | (JP) . |
| 8800350 | | 9/1989 | (NL) . |

OTHER PUBLICATIONS

Fitten, Am. J. Psychiatry 147, 239, Feb. 1990.*
Molloy, Can Med. Assoc. J. 144(1), 29, Jan. 1991.*
Wilcock, Age and Ageing 22, 316, 1993.*
Weinstein, J. Neurology 238, 34, 1991.*
Claman, Alz. Dis. and Associated Disorders 5, Suppl 1, S49, 1991.*
F–D–C Reports ("The Pink Sheets") 53(12) 1, 4–9, Mar. 25, 1991.*
Thal, "Alzheimer Disease" (Terry, Ed, RAven Press, NY) pp. 431–444, 1994.*
"FDA" New England Journal of Medicine 324(5), 349, Jan. 31, 1991.*
Letters from Pirozzolo and Others, New England Journal of Medicine 346(25), 1603, Jun. 18, 1987.*
Gauthier, New England Journal of Medicine, 322(18) 1272, May 3, 1990.*
Davis, New England Journal of Medicine, 327(18) 1253, Oct. 1992.*
Davies, The Lancet Jul. 15, 1989, p. 163.*
Chatellier, BMJ 300, 495, Feb. 24, 1990.*
Levy, The Lancet Feb. 7, 1987, p. 322, Feb. 7, 1987.*
Letters by Wilcock and others, BMJ 300, 939, Apr. 7, 1990.*
Harbaugh, Ann. NY Acad Sci 531, 174–9, 1988.*
Penn, Neurology 38, 219, Feb. 1988.*
Abstract of US 4713376, Dec. 1987.*
Abstract of US 4735944, Apr. 1988.*
Abstract of US 4701407, Oct. 1987.*
Abstract of US 4680172, Jul. 1987.*
Abstract of US 4661500, Apr. 1987.*
Abstract of US 4737499, Apr. 1988.*
Abstract of US 4665056, May 1987.*
Abstract of US 4748154, May 1988.*
Abstract of US 4469707, Sep. 1984.*
Abstract of US 4734275, May 1988.*
Abstract of US 4690949, Sep. 1987.*
Abstract of US 4481206, Nov. 1994.*
Becker, ed, Alzheimer Disease: From Moleculkar Biology to Therapy, pp. 579–584, 1996.*
Eagger, Dementia 2, 207, 1991.*
Gauthier et al in Current Reasearch in Alzheimer Therapy: CHolinesterase Inhibitors, pp. 237–235, 1988.*

(List continued on next page.)

Primary Examiner—Mark L Berch
(74) Attorney, Agent, or Firm—Ladas & Parry

(57) ABSTRACT

Compounds of the formula

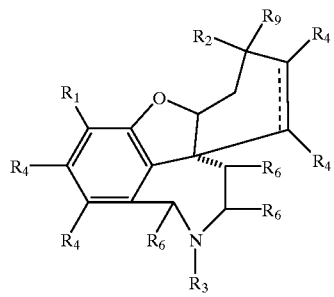

wherein the broken line represents an optionally present double bond, and $R_1$–$R_3$, $R_4$, $R_6$ and $R_9$ are as defined herein, and compositions containing these compounds can be used to inhibit acetylcholinesterase activity and treat Alzheimer's Disease.

67 Claims, No Drawings

OTHER PUBLICATIONS

Aricept NDA 20–690 Document History, pp. 3,34,35,61–64, 1996.*
Rogers, Neurology 50, 136, Jan. 1998.*
Guy, ECDEU Assessment Manual for Psychopharmacology, Revised 1976, pp. 218–222, 1976.*
Summary of Basis for Approval of NDA 17–993 (Hydergine) Nov. 1977.*
PDR, 52nd Edition, p. 14, 1998.*
http://www.planetrx.com/product/rx/shelf/info/1088_introduction.asp (Hydergine), Undated.*
PDR 49th Edition, pp. 1826–1830, 2162–2163, 1995.*
Knapp, JAMA 271, 985, Apr. 1994.*
Kluger, Psychiatric Clinics of America vol. 14, 309, Jun. 1991.*
Welsh, Abstract of Arch Neurol 49, 448, May 1992.*
http;//www.phrma.org/issues/lead.html, Undated.*
Kewitz, ed, Phram. Interventions on Cent. Cholinergic Mech. in Senile Dementia, pp. 233–237, 1989.*
Diagnostic and Statitical Manual of Mental Disorders (3rd Ed, Revised), pp. 119–121, 1987.*
Joachim, Ann. Neurology 24, 50–56, 1988.*
Abstract for J. Neurolo Sci 95(3), 239–258, Mar. 1990.*
Bergener, Ed, Diagnosis and Treatment of Senile Dementia, pp. 164–173, 1989.*
Giacobini, ed, Alzheimer Disease: Therapeutic Strategies, pp. 140–144, 1994.*
Pontecorvo, 6th Int. Conf On Alzheimer's Dis & Related Disorders Abstract 26, p. S7 and Slide, Jul. 1998.*
Kewitz, First European Cong. of Pharmacology, unnumbered page, 1988.*
Partial Abstract of Script #1948 p. 21, 1988.*
Jenden, Ed, Cholinergic Mechanisism and Psychopharmacology, pp. 125–137, 1977.*
Massoulie, Ann. Rev. NeuroSci. 5, 57–106, 1982.*
Goodmanand Gillman Pharmaceutical Basis of Therapeutics, 6th Ed, pp. 56–90, 1980.*
Sherman, Alzheimer Disease and Associated Disorders 2(3) p. 216, 1988.*
Liston, Alzheimer Disease and Associated Disorders 2(3) p. 219, 1988.*
Thal, J. Am. Geriatric Society 37: 42–48, 1989.*
Stern, Ann. Neurology 22, 306, 1987.*
Jenike, J. Clin Psychiatry 51:3–7, 1990.*
Harrell, J. Am. Geriatric Society 38, 113, 1990.*
Iqbal, Ed, "Alzheimer's Disease and Related Disorders" (Alan Liss, Inc, New York) pp. 1291–1299, 1989.*
Abdallah, Phytochemistry vol. 39, 477, 1995.*
Sarter, Psychopharmacology 107, 144–159, 1992.*
Han, Eur. J. Med. Chem 27, 673–687, 1992.*
Daleva, Eksp Med. Morf. 1963 1:38–46 from Abstract Bulg. Sci. Lit. Med. Phys. Cultur. 6(3) Abstract 359 (1963) Translation submitted.
J. R. Boissier, et al. CA56, 2515a (1962.
R.D. Penn, et al. Neurology (1988) 38:219–222.
Friedman, et al. Nature Medicine (1996), Dec. 2 (12):1382–5 (Abstract).
Benjamin Calesnick, Chapter 6 of Drill's Pharmacology in Medicine (1971), pp.:99–124.
Sweeney, Bachman and Coyle's, Psychopharmacology (1990), 102:191–200.
Rodda, et al., Biopharmaceutical Statistics for Drug Development (1988), Chapter 6, pp. 273–328.
Goodman and Gilman, The Pharmacological Basis of Therapeutics, 1996, pp. 55–58.
Bayer Website, Mar. 17, 1998, Spring Financial News Conference of Bayer AG, "1997: A Year of Exceptional Growth at Bayer".
Doctor's Guide Website—Galantamine Improves Memory and Learining Ability in Alzheimer's Patients, 1998—Janssen Press Release. (Jul. 20, 1998).
P. Dal–Bianco, et al. Galanthimine Treatment in Alzheimer's Disease, Presented at the 19th Central European Neurobiological Sypmposium–CNS–19, Vienna, Jun. 29–Jul. 1, 1989.
Pontecorvo, et al. Slide presented at the 6th International Conference on Alzheimer's Disease and Related Disorders, Amsterdam, Jul. 18–23, 1998.
Summers, et al. The New England Journal of Medicine (1986), vol. 315 (20): 1241–5.
Knapp, et al. JAMA, Apr. 6, 1994, vol. 271, No. 13, pp. 985–991.
Vincent, et al., Abstract. 237.4. Society for Neuroscience 1987.
Zhang, et al., Chung Kuo Yao Ki Hsueh Pao (1991) 12 (3):250–2 (Abstract).
Xu, et al., Chung Ko Yao Li Hsueh Pao (1995), 15(5), 391–5 (Abstract).
Nelson, P., "Table of Contents for AD Diagnosis and Treatment Guide," last updated Sep. 8, 1998.
W.N. Aldridge, et al., Acta. Pharmacol. et. Toxicol., 1981, 49, Suppln. V. 3–6.
Anon, New Chemicals Markedly Inhibit Cholinesterase, Government Reports, Announcements and Index, Issue 23, 1986.
I. Kimura, et al., Japanese J. Pharmacology, 1993 May, 62(1):35–41 (Abstract Only).
Wall Street Journal, Sep. 28, 1998, p. 1.
Bores, et al., The Journal of Pharmacology and Experimental Therapeutics, Vo. 277, No. 2, pp. 728–738.
Davidson, et al., Biol. Psychiatry, 1988 (23): 485–490.
Davis, et al., Am. J. Psychiatry, 144:4, Apr. 1987, pp. 468–471.
Gibson, et al., Lancet, Mar. 23, 1985, pp. 695–696.
Sharpless and Thal. Lancet, Jun. 15, 1985, pp. 1397–8.
Somani and Khalique, J. Anal. Toxicol. (1985), 9:71–75.
Thal. et. al. Ann. Neurol. (1983) 13:491–496.
Lamb, et al. , Drugs and Aging, 1997 Dec. 11 (6), pp. 490–496.
Scrip 1875, p. 12. (Nov. 23, 1998).
Vincent, Abstract No. 27.12, Society for Neuroscience, 1988.
Sweeney, et al., Psychopharmacology (1990) 102:191–200.
Bores, et al., Drugs of the Future, 1996, 21 (6):627–636.
Abstract of Cummings, Neurology 50 p 1214 (1998.
Abstract of Rogers, Neurolog 50, p. 136 (1998).
J. Corey–Bloom, International Journal of Geriatric Psychopharmacology (1998) Abstract only.
M. Farlow, JAMA, Nov. 11, 1992, vol. 268, No. 18, pp. 2523–2529.
Recent News, Novartis Website, May 13, 1998.
Bhasker, P.A. "Medical management . . . " Antiseptic, vol. 71, No. 1 pp. 45–47. (1974.
Bubeva–Ivanova, L. "Amaryllidaceae alkaloids . . . " Chemical Abstracts, vol. 57, (1962) abstract No. 12560e, Columbus, Ohio.

Combes, G. et al. "Galanthaminone" Chemical Abstracts, vol. 58, (1963), Abstract No. 1141b, Columbus, Ohio, pp. 1805–1809.
Laiho, S.M. et al. "Narcissamine . . . " Chemical Abstracts, vol. 61, (1964), Abstract No. 14732f.
Koizumi, J. et al. "Galanthamine . . . " Chemical Abstracts, vol. 61, (1964) & Chem. Pharm. Bull. (Tokyo) 12(6), 696–705(1964).
Abdusamatov, A. et. al. "Alkaloids from Ungernia . . . " Chemical Abstracts, vol. 59, (1963) abstract No. 3716f, Columbus, Ohio. S. Dokl. Akad. Nauk. UZ. SSR 20(1), 1821 (1963).
Minami, S. et al. "Galanthamine . . . " Chemical Abstracts, vol. 61, (1964), abstract No. 14727g S. Chem. Pharm. Bull. (tokyo) 12(9) 1012–20 (1964.
Kametani, T. et al "Synthesis of heterocyclic . . . " Chemical Abstracts, vol. 74, (1971) abstract 1122652, Columbus, Ohio. & J. Chem. Soc. C. (1971), (3) 590–2.
Kametani, T. et al. "Syntheses of Analgesics . . . " Chemical Abstracts, vol. 78, (1973) p. 507, abstract No. 11158 T, Columbus Ohio, US & J. Heterocycl. Chem. (1973), 10(1), 35–7.
Chemical Abstracts, vol. 77, 1972, p. 515, abstract No. 48690S, Columbus, Ohio, & JPA–72 13 919 (Grelan Pharmaceutical Co. Ltd) (26–04–72).
Kametoni, T. et al. "Syntheses of narwedine–Type enones . . . "Chemical Abstracts, vol. 77, (1972) p. 526, abstract No. 62186p. Columbus Ohio. & J. Chem. Soc. (1972) pp. 1513.
Schultz, A.G. et al. "Total synthesis . . . " Chemical Abstracts, vol. 88, (1978), p. 612 abstract No. 7146c, Columbus, Ohio, & Am. Chem. Soc., (1977) 99(24), 8065–7.
Cecchini, M. "Treatment of Motor . . . " Chemical Abstracts, vol. 66, 1967, p. 8772, abstract No. 93920a, Columbus Ohio & Minerva Med. 57(83) 3385–6 (1966).
Manske, R.H.F."The Alkaloids . . . " vol. VI, (1960), Academic Press, N.Y. pp. 348–352.
Comfort, A "Cholinesterase . . . "The Lancet, vol. 1, No. 8065, (1978) pp. 659–660.
Baraka, A. et al. "Reversal of central . . . " J.A.M.A., vol. 238, No. 21, 21st. (1977) pp. 2293–2294.
Chablygina et al Z.H VISSH. Neru, Deint., vol. 26, (1976) pp. 1091–1093.
Brufani, M. et al. "A long–lasting cholinesterase . . . " Pharmacology Biochemistry & Behavior vol. 26, No. 3, (1987) pp. 625–629.
Liston et al, "Alzheimer Disease & Related Disorders" vol. 2(3) 1988, p. 219.
Sun et al, Soc. Neurosci Abs. 14, unpaginated page, 1988.
Coata et al, Soc. Neurosci Abs 15, #463,10 (1989).
Robinson, Br. J. Pharmacol. 98, 1127 (1989).
Chaplygina, Zh Vyssh. Nerv. Deint 26, 109(1976) and Translation.
Minami *Chemical Abstracts,* vol. 61, No. 12, Dec. 7, 1994, 14727g.
Koizumi *Chemical Abstracts,* vol. 61, No. 11, Nov. 23, 1964, 13357 and 13358
Kametami *Chemical Abstracts,* vol. 74, No. 21, May 24, 1971, pp. 423–424 112265.
Schultz *Chemical Abstracts,* vol. 88, No. 1, Jan. 2, 1978, pp. 611–612, Abstract No. 7146c.
Laiho, S., et al., "Narcissamine. Aquasi–Racemic Alkaloid", *J. Am. Soc.,* vol. 86, No. 20, Oct. 20, 1964, pp. 4424–4288.

Kametanl, T., et al., "Studies on the Syntheses of Heterocyclic Compounds. Part CDLXVI, Synthesis of Narwedine–type Enones by Photochemical Cyclisation", *J. Chem. Soc. Perkin Trans.,* vol. 12, 1972, pp. 1513–1516.
Comfort, A., "Cholinesterase Inhibition In Treatment Of Alzheimer's Dementia", *The Lancet,* vol. 1, No. 8065, Mar. 25, 1978, pp. 659–660.
Hollander, Biol. Psy. 22, 1067 (1987).*
Davidson, Biol. Psy. 23, 485 (1988).*
Bareh, Abstract for Int. J. Psy Nect. 17, 193 (1987).*
Fillenbaum, Abstract for Arch. Neurol 44, 924 (1981).*
Magazena, Abstract for J. Am Geriatric Soc 35, 996(1987).*
Teng, Abstract for J. Clin Psychiatry 48, 314 (1987).*
Fisk, Abstract for J Am Geriatric Soc 35, 307.*
Bird, Abst for J. Nerv. Mental Dis 175, 731 (1987).*
Villardita, Abs for J Neural Transm Suppl 24, 293 (1987).*
Zubenko, Abs for J. Neuropath Exp Ther 46, 407 (1987).*
Haff, Abst for Neurology 37, 1119(1987).*
Selnes, Abst for Neurology 38, 1053(1988).*
Kessley, Abst for Z Gerontol 21, 38(1988).*
McKhann, Neurology 34, 939 (1984.*
Bird et al, "Current Communication in Molecular Biol, Cold Spring Harbor", 169–173 (1988).*
Amano, Abs for *No To Shinkei,* 36(7) 657 (1984).*
Powell, Abs for J. Neurogenet 1, 189 (1984).*
"Goodman & Gillman's The Pharmaceutical Basics of Therapeutics", 1985 7th Edition pp. 49–65.*
Casanva, Abstract for Ann. Neurol 18(3), 310 (1985).*
Wisniew Ski, Abstract for Ann Neurol 17(3), 278 (1985).*
Mildwaf, Abstract for Ann Neurol 22, 275 (1987).*
Tanzi, Abstract for Nature, 329, 156 (1987).*
Ball, Abstract for Ann Neurol 7, 462 (1980).*
Wisniew Ski, Abs for Neurology, 35, 957 (1985).*
Wade, Jr. "Organic Chemistry" (2nd Edition) 1992, p. 825.*
Cutler, Abs. for Ann. Int Med. 103, 566–78 1985.*
Fessander, "Organic Chemistry" (3rd Edition) 1991 pp. 731–735, 739, 741–742, 756–757.*
Hollander British Med Bull 42, 97 (1986).*
Lebu, "Guidelines for Clin. Eval. of Antidementia Drugs, First Draft" (11–90).*
Davis, Am. J. Psy 144, 468 (1987.*
Wurtman et al. "Proc. $3^{rd}$ Meeting of Int. Study Group on Treatment of Memory Disorders Associated with Aging", Zurich Switzerland Jan. 13–15, 1984, pp. 391–405, pp. 333–347.*
Kennard et al, Nature Medicine 2, 1230 (1996).*
Wade, Arch Neurol 44 24 (1987.*
Martin, Abstract of Neurology 37, 1201 (1987).*
Joachim, Abstract of Ann Neurol 24, 50 (1988).*
Mendez, J. Geriatric Psy. & Neurology 4, 26 (1991).*
Forsyth, Clin Pharmacology & Therpeutics 46, 634 (1989).*
Laston, Alz. Dis & Relat. Disorders 2, 43, p. 219.*
Griffith, Abstract of J. Pharmacol & Exp Ther 255, 1986 (1990.*
Jossan, Pharmacol & Toxicol 71, 231 (1992).*
Abstract of R & D Focus Drug News, Aug. 26, 1996.*
Pink–Sheet of Sep. 30, 1996, p. 9.*
"Interneuron Company Profile", Script–Online–plus, Aug. 16, 1995.*
Script 1784, "Review–Issue 1992", p. 18.*
Rosen et al, Am. J. Psychiatry 141, 1356 (1984).*
Folstein, J. Psychiatrie Res 12, 189 (1975).*
McKhann, Neurology 34, 939 (1984).*
Schoenberg, Ann. Neurol 22, 724 (1987).*

Davis, Lancet 345, 625 (1995).*
Hon, European J. Med. Chem 27, 673–687 (1992.*
Haginaka, J. Chromatograph 577, 95 (1992).*
"Goodman & Gillman's Pharmaceutical Basis of Therapeutics " 9$^{th}$ Ed. (Hardmon, Ed) (McGraw Hill, 1996), pp. 105–111, 141–160, 199–225, 240–248, 249–258, 262–263, 361–380, 393–396, 1769, 1784, 431–446, 455–459, 491–496, 501–502, 581–586, 592–593 598–600, 659–665, 672–674, 679–682, 684–888, 895–897, 1447–1450, 1455–1457.*
Sweeney, Pharmacol. Biochem. & Behavior 31, pp. 141–147 (1988).*
McGeer, Abstract only of "Can J. Neurol. Sci 13, 511–6 (1986)".*
Simonic, Zupan, "Interdisciplinary Sattelite Symposium to the IV World Conf. on Clin. Pharm. & Thera. " (Berlin Jul. 28–30, 1989) #34&35.*
Waldholz, "Wall Steet Journal" Aug. 8, 1989.*
Cozanitis, Nouv. Presse Med 1978, vol. 7 p. 4152 with translation.*
Smith et al, Lancet, p. 42 of issue of Jan. 6, 1979.*
Merch Manual, 14$^{th}$ Edition, 1982, pp. 1305–1309.*
Kraus, Chem Abs 81, 72615z (1974).*
Göpel, Psychiat. Neurol Med. Psychol. 23, 712–718 (1971).*
Hoaroutunian, Abstract of "Can J. Neurol. Sci 1986, 13, 385–93".*
Bishop, Wall Street Journal Aug. 21, 1989, p. B1.*
"Science News", issue of Jul. 29, 1989 p. 68.*
Fary, N.Y. Times Nov. 10, 1989, p. 1 "Study Finds . . . ".*
Newman, Wall Street Journal, Nov. 10, 1989, "Alzheimers might be . . . ".*
McLachlan, Chem Abs 109, 40492 (1987).*
Martyn, Chem Abs 110, 130078.*
Schmeck Jr, New York Times, Apr. 11, 1989 "New Findings Offer clues . . . ".*
Manuelidis et al, Proc. Natl. Acad. Sci. USA 85, 4898 (Jul. 1988).*
Zakirov, Chem Abs 77, 109452.*
Losev, Chem Abs 103, 625c (1985).*
Boit, Chem Abs 51, 8120f (1956).*
Kobayashi I, Chem Abs 85, 160383K (1976).*
Kobayashi II, Chem Abs 95, 25351 (1900).*
Marx *Science 249,* pp. 954–985 (1990).*
Thompson New Eng J. Medicine 323, 445–448 (Aug. 1990).*
Marx II, Science 250 1509 (Dec. 14, 1990).*
Ighal, et al, "Alzheimer's Disease and Related Disorders" (Liss, Inc) pp. 135, 260 (1989).*
Beal, in "Harrison's Principle of Internal Medicine", pp. 2060–2062, 2036–2037, p. 2071.*
Ranier, et al in "Pharmacological interventions in Senile Dimentia", pp. 233–236 (1989).*
Abstract of Allen, Neuroscience Letters 131, 135–9.*
Abstract of Olso, J. Neur. Transm. Park Dis 479 (1992).*
Abstract of Batcher, "Neuorbiol Aging"; 10, 557 (1990).*
Abstract of Mufson, Exp Neurol 105, 221–32 (1989).*
Kewitz, "Alzheimer's Disease: Therapeutic Strategies" (Birkhauser, Boston, 1994) pp. 140–144.*

* cited by examiner

GALANTHAMINE DERIVATIVES FOR TREATMENT OF ALZHEIMER'S DISEASE

CROSS REFERENCE TO RELATED APPLICATION

This application is a continuation of application Ser. No. 08/139,338 filed Oct. 19, 1993 which is a continuation of application Ser. No. 07/781,028 of Oct. 18, 1991 now abandoned. Application Ser. No. 07/781,028 is a continuation-in-part of applications Ser. No. 07/695,949, of May 6, 1991 now abandoned and Ser. No. 07/046,522 of May 4, 1987 now abandoned. Application Ser. No. 07/695,949 is itself a continuation of application Ser. No. 07/541,076 filed on Jun. 21, 1990 which is a continuation of application Ser. No. 07/219,914 filed on Jul. 15, 1988 now abandoned which is in turn a continuation-in-part of application Ser. No. 07/046,522 filed on May 4, 1987 now abandoned.

The present invention is directed to galanthamine-analogues having cholinesterase inhibiting properties and their preparation and use for treatment of Alzheimer's disease and related dementias, some of the analogues are novel.

U.S. Pat. No. 4,663,318 issued on May 5, 1987 describes the use of galanthamine for the treatment of Alzheimer's disease and related dementias.

Published European Patent Application 236684 describes the use of galanthamine and certain analogues for the treatment of Alzheimer's disease and related dementias, such analogues are those wherein the hydroxy group of naturally occurring galanthamine may be replaced by methoxy, ethoxy or lower alkanoyloxy, the methoxy group of galanthamine may be replaced by hydrogen, methoxy, ethoxy or lower alkanoyloxy and the N-bonded methyl group may be replaced by other straight or branched chain alkyl groups, cyclopropylmethyl, cyclobutylmethyl or allyl groups or substituted lower alkyl phenyl groups or wherein other hydrogen atoms are substituted by chloro or fluoro atoms.

The literature shows the epigalanthamine wherein the hydroxy group is in the equatorial position so that hydrogen bond stabilization of structure is not possible has an anticholinesterase activity of only 10% of galanthamine. (Chem. Abstr., 77, 109461s)

A number of galanthamine analogs occur naturally or have been obtained from natural products including the following compounds described in the text book The Alkaloids (edited by R. H. F. Manske published by Academic Press, N.Y., 15th Edition):

narwedine:
(also referred to sometimes as galanthaminone)

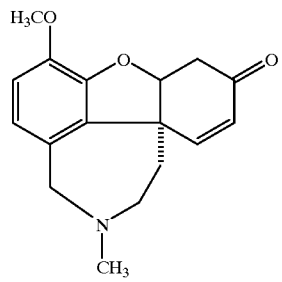

Narwedine has been reported to have weak anticurare activity at 3 mg/kg (Chem. Abstr., 78, 131941r) and to have cholinergic effects on respiration and heart activity, 50–80% lower than galanthamine (Chem. Abstr., 80, 103864r), Schmidt et al in Acta. Biol. Ned. Ger. 7: 402–410 (1961) report that the anticholinesterase activity of Narwedine is less than 1% of that of galanthamine.

(-) N-demethylgalanthamine:

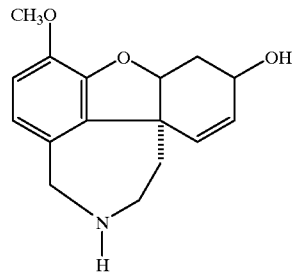

galanthamine-O-methyl ether:

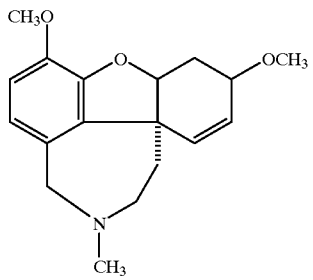

childanthine:

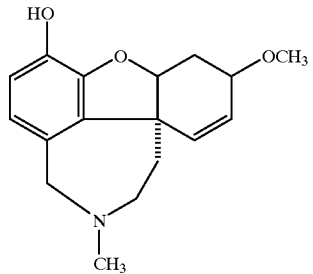

lycoramine:

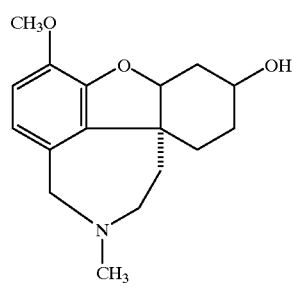

It has been reported that the concentration of lycoramine required to stimulate EEG—recorded activity is about five times that required for galanthamine (Chem. Abstr., 62, 15306e). deoxylycoramine

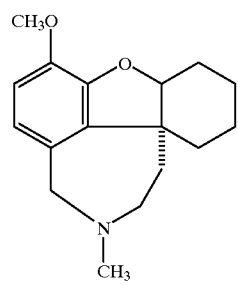

habranthine:

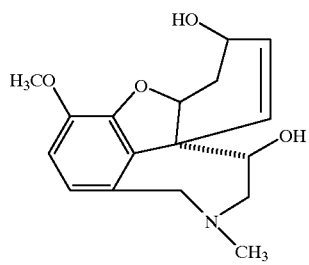

anhydrogalanthamine:

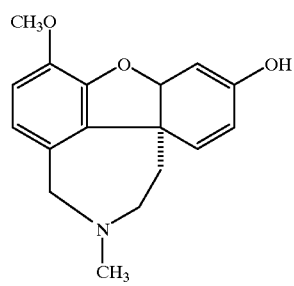

anhydro-O-demethylgalanthamine:

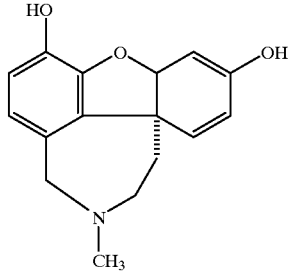

and N-mesityl and N-benzyl derivatives of galanthamine. Reference is also made to compounds of the formulae:

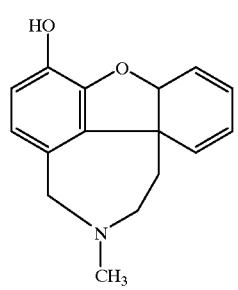 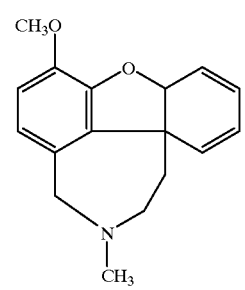

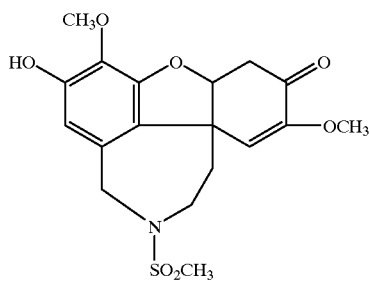

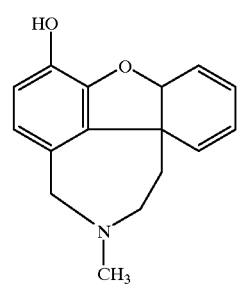

The latter compound has been reported to have activity similar to that of galanthamine (J. Chem. Soc., (C) 1043 (1971).

An earlier edition The Alkaloids (R. H. F. Manske editor, Academic Press) of this book had also referred to (+) N-demethyldihydrogalanthamine of the formula:

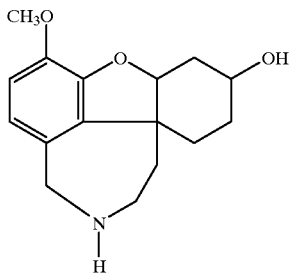

N-Desmethyldihydrogalanthamine is described by Kametani et al in J. Heterocyclic Chem., 10, 35–37 (1973). The same paper also refers to galanthamine O, N-diacetate leucotamine

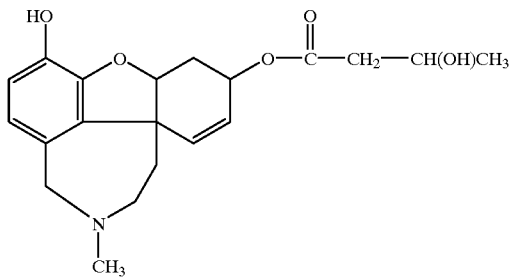

and its O-methyl and O-methyl acetic acid ester are described by Kobayashi et al in Chem. Pharm. Bull., 33:, 5258–5263 (1985).

O-Desmethyldihydrogalanthamine (also known as O-demethyllycoramine) and O-demethylgalanthamine (sanguinine) are also described by Kobayashi et al in Chem. Pharm. Bull., 28:, 3433–3436 (1980).

Subsequently, Kobayashi disclosed the extraction of O-demethyl lycoramine (also known as dihydrosanguinine) from bulbs of Lycoris radiata Herb. (Chem. Pharm. Bull., 28: 3433–6 (1980), Chem. Abstr. 95,25351.

A bromo-narwedine of the formula:

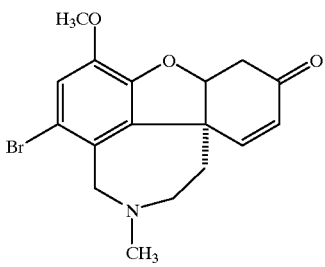

is described as an intermediate in the synthesis of galanthamine by Kametani et al in Chem. Comm., 425 (1969) and J. Chem. Soc. (C), 2602 (1969).

Chem. Abstr. 61,14727g Chem. Pharm. Bull., 12:1012–20 (1964) describes the production of compounds of the formula:

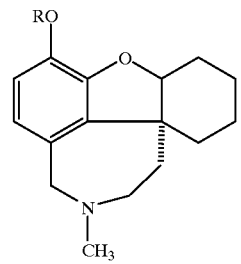

wherein R may be hydrogen, methyl or ethyl.

A dihydro derivative of childanthine obtained by hydrogenation of the parent compound is described by Boit in Chem. Ber, 90: 57–9 (1957): Chem. Abstr., 51,8120f.

Chemical Abstracts 81 638193 describes n.m.r. studies on dihydrogalanthamine and its acetic acid esters.

Fales, Giuffrida and Wildman in Journal of American Chemical Society, 78:4145 (1956) report that the bulbs of King Alfred daffodils contain the known alkaloids galanthamine, galanthamine, lycoramine, haemolycoramine, haemanthamine and narcissamine and a new alkaloid pseudo lycorine. They also reported that narcissamine has been shown to be N-demethyl galanthamine.

Latho and Fales in J. Am. Chem. Soc., 4434–4438 (1964). report that contrary to what had previously been believed, narcissamine was in fact a mixture of N-demethylgalanthamine and N-demethyllycoramine.

Tetsuji Kametani et al. in Yakuyaku Zasshi 12: 1353–1358 (1977) describe a synthetic route to convert 2-benzazepin-3-ones to galanthamine analogues in anticipation of them having analgesic activity. Among the analogues including those where the phenol ring is substituted by bromine or hydroxy methyl on the carbon atom adjacent to the phenolic hydroxy group.

In German OS 2945161 there is described the production of certain narwedine type enones and their derivatives, including those where the benzene ring is bromo-substituted and the nitrogen containing ring contains a keto group adjacent to the nitrogen.

Shimizu et al in Heterocycles, 8: 277–282 (1977) (abstracted in Chemical Abstracts, 88, 136821t) describe certain narwedine derivatives used as intermediates having the following formulae:

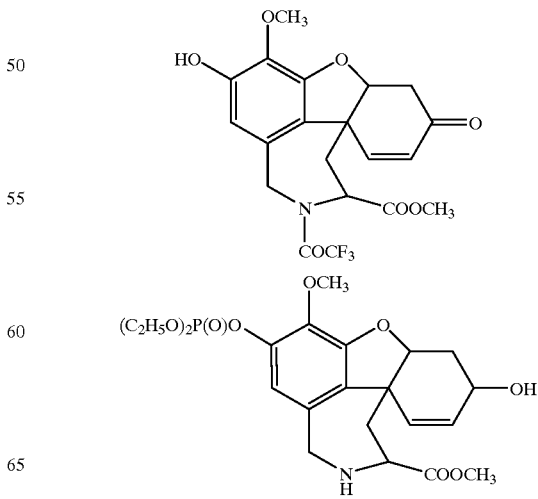

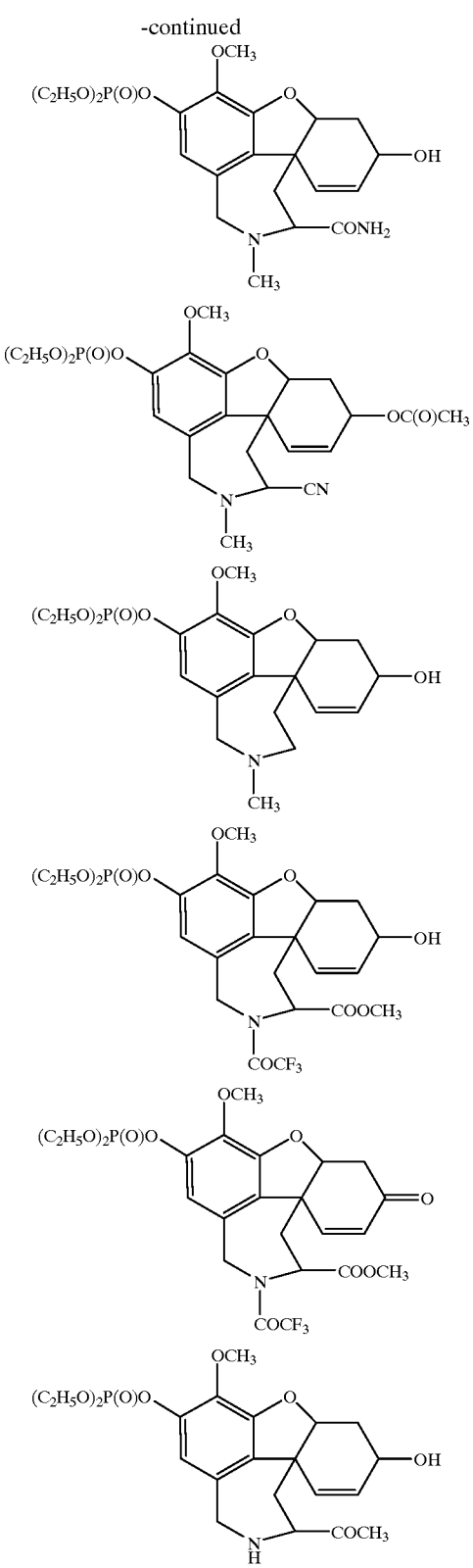

Irwin and Smith in Arch. Int. Pharmacodyn., 127:314–330 described the cholinesterase activity of galanthamine and some of its analogues including lycoramine acetate methiodide, neopin methiodide (both of which were ineffective) and deoxydemethyl lycoramine methiodide (which demonstrated good activity) and deoxylycoramine (which exhibited some activity). It was hypothesized that the presence of a free hydroxy group in the cyclohexane ring conferred activity on the molecule since the acetylation of this group led to a drop in activity.

In J. Pharm. Exp. Ther., 134:53 (1961), Irwin, Smith and Hein expanded on the work just described and reported that replacement of the hydroxyl group of deoxydemethyl lycoramine methiodide by a carbamate group resulted in useful pharmacological activity.

Subsequently, Irwin and Hine, J. Pharm. Exp. Ther., 136:20 (1962) described the activity of a number of carbamates including deoxydemethyl lycoramine carbamate on cholinesterase activity in rat brain.

Subsequently, Somers et al. in Neurology, 13:543 (1663) reported that some of Irwin's compounds were useful in treating myasthenia gravis.

One of the characteristics of Alzheimer's disease and certain other considerations is a reduction in the amount of acetyl choline in the brain (see for example, Perry et al British Medical Journal 2:1457–1459 (1978). Acetylcholine is a compound that is involved in the transmission of electrical impulses between nerve endings. Excessive amounts of acetyl choline cause undesirable side effects so that the brain also contains a cholinesterase enzyme to prevent build up of acetyl choline. Thus, if the production of acetyl choline cannot be increased, one way to approach the problem of low acetylcholine levels is to reduce the amount or activity of the cholinesterase so that such acetyl choline is present may be used. Unfortunately, finding a useful treatment for Alzheimer's disease is not simply a matter of feeding a patient with a cholinesterase inhibitor. To be effective, a compound must pass the blood brain barrier easily and distribute itself between the central and peripheral nervous systems in such a way that its effect is mainly central, and it must not have significant side effects. It must have a reasonably long half life in the brain. It must be reversible to at least some extent (otherwise nerve gasses would be effective treatment—which they are not) and it must be able to be formulated in a way that makes it suitable for use by those suffering from the disease. Loss of acetyl choline in the brain can exist alongside other conditions where Alzheimer's disease is not the primary indication where the same neurochemistry exists. References herein to "related dementias" are intended to include to such situations. Similar problems of cholinergic deficiency and dementia accompanied by plaques and tangles in the brain also arise in the later stages of Down's syndrome which is similarly a "related dementia".

DETAILED DESCRIPTION OF THE INVENTION

From one aspect, the present invention relates to the use of compounds of the formula I to treat Alzheimer's disease and related dementias wherein the broken line represents an optionally present double bond in one of the two portions shown, $R_1$ and $R_2$ are each selected independently from the group consisting of hydrogen, hydroxyl, amino or alkylamino or phenyl amino, cyano, sulfhydryl, alkoxy preferably of 1–6 carbon atoms, alkylthio, aryloxy, arylthio, $R_5$-substituted aryloxy, $R_5$-substituted arylthio, aryloxy, aralkylthio, $R_5$-substituted aralkoxy, $R_5$-substituted aralkylthio, aryloxymethyl, $R_5$-substituted aryloxymethyl, alkanoyloxy, hydroxy-substituted alkanoyloxy, benzoyloxy, $R_5$-substituted benzoyloxy, aryloxy carbonyl and $R_5$-substituted aryloxy carbonyl and corresponding carbonates, a mono or dialkyl or aryl carbamate group, or hydroxy methyl, $R_1$ may also by alkyl of up to 14 carbon atoms, $R_2$ may also be halo such as iodo or may be carboxymethyl provided that at least one of $R_1$ and $R_2$ is hydroxy, amino or alkylamino unless $R_7$ or $R_8$ is hydroxymethyl, $R_3$ is hydrogen, straight or branched chain alkyl, preferably of 1–6 carbon atoms, cycloalkyl methyl, alkylphenyl, $R_5$-substituted alkylphenyl, heterocyclic such as α- or β-furyl, α- or β-thienyl or thenyl, pyridyl, pyrrolyl pyrazinyl or pyrimidyl -groups, alkyl heterocyclic and R'-substituted heterocyclic, where R' is alkyl or alkoxy or $R_3$ is alkanoyl of 1 to 8 carbon atoms or aroyl wherein the aryl group is of 6 to 10 carbon atoms, the alkyl and aryl portions of said groups optionally being substituted by $R_5$ groups as hereinafter defined or $R_3$ is the residue of a compound having adrenergic or monoamino oxidase activity and is selected from the group consisting of a)

wherein Hal is a halogen, preferably chloro, p is 0, 1 or 2, q is 0 or 1, r is 0 or 1 and Z is selected from the group consisting of i)

wherein Q is hydrogen or hydroxy, L is hydrogen or $C_{1-4}$ alkyl, G is hydrogen, $C_{1-4}$ alkyl, alkylphenyl wherein said phenyl group is optionally substituted by hydroxy or methylene deoxy, or is alkyl alkanylamino ii)

wherein G is as defined above, iii)

iv)

v)

b)

c)

—CH$_2$—CH$_2$NH NH$_2$ and d)

each $R_4$ is independently selected from hydrogen, hydroxyl, sulfhydryl, alkyl, aryl, aralkyl, alkoxy, thioalkoxy, aryloxy, thioaryloxy, alkylarlyoxy, alkylmercaptoaryloxy, nitro, amino, N-alkylamino, N-arylamino, N-alkarylamino, fluoro, chloro, bromo iodo and trifluoromethyl, and Rx is selected from the same groups as $R_4$, $R_6$ is hydrogen, halo, trifluoromethyl or alkyl of 1 to 4 carbon atoms, $R_7$ is selected from the same groups as $R_4$ or may be hydroxy alkyl of 1–2 carbon atoms, $R_8$ is hydrogen or hydroxymethyl, $R_9$ is hydrogen, alkyl of 1 to 6 carbon atoms, phenyl or benzyl, or when $R_2$ is hydroxyl $R_9$ may be a moiety of formula I wherein $R_9$ is hydrogen and $R_2$ is a linking bond; or $R_2$ and $R_9$ may jointly form a semicarbazone, oxime, phenylhydrazone or a keto group X is oxygen or $NR_5$, Y is nitrogen, and methylenedioxy derivatives thereof with the proviso that when X is O, $R_3$ is not methyl when $R_1$ is methoxy, $R_2$ is hydroxy, and all $R_4$ are hydrogen or a pharmaceutically-acceptable acid addition salt thereof. When there is no unsaturation in the 1,2 carbon bond, $R^2$ is preferably oriented axially to the cyclohexane ring. When R and $R_9$ jointly form a single group it is normally desirable that $R_1$ be hydroxy or amino.

Compounds of formula I are also where $R_1$ and $R_2$ are each selected independently from the group consisting of hydrogen, hydroxyl, amino, phenylamino, alkylamino, cyano, sulfhydryl, alkoxy of 1–6 carbon atoms, alkylthio, aryloxy, aralkoxy, $C_{1-6}$ alkyl carbonate or $R_5$-substituted phenyl or benzyl carbonate, $R_5$-substituted aryloxy, $R_5$-substituted arylthio, aralkoxy, an aliphatic or aryl carbamate group wherein the aliphatic or aryl moiety may be $R_5$-substituted or unsubstituted, aralkylthio, $R_5$-substituted aryloxymethyl, alkanoyloxy, hydroxy-substituted alkanoyloxy, benzoyloxy, aryloxy carbonyl, $R_1$ may also be alkyl of up to 14 carbon atoms, or hydroxymethyl, $R_2$ may also be carboxymethyl provided that at least one of $R_1$ and $R_2$ is hydroxy, amino or alkylamino unless $R_7$ or $R_8$ is hydroxymethyl, $R_3$ is hydrogen, straight or branched chain alkyl of 1–6 carbon atoms, cycloalkylmethyl, phenyl, $R_5$-substituted phenyl, alkylphenyl, $R_5$-substituted alkylphenyl, heterocyclic selected from α- or β-furyl, α- or β-thienyl or thenyl, pyridyl, pyrazinyl and pyrimidyl, alkyl heterocyclic or R'-substituted heterocyclic where R' is alkyl or alkoxy and heterocyclic is selected from or α- or β-furyl, thienyl, thenyl, pyridyl, pyrazinyl, pyrimidyl or methylpyrryl, $R_3$ is alkanoyl of 1 to 8 carbon atoms or aryl wherein the aryl group is of 6 to 10 carbon atoms, the alkyl and aryl portions of said groups optionally being substituted by $R_5$ groups as hereinafter defined or $R_3$ is the residue of a compound having adrenergic or monoamino oxidase activity and said residue being selected from the group consisting of a)

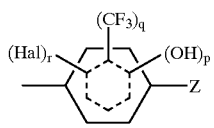

wherein Hal is a halogen, p is 0, 1 or 2, q is 0 or 1, r is 0 or 1 and Z is selected from the group consisting of i)

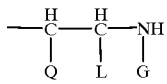

wherein Q is hydrogen or hydroxy, L is hydrogen or $C_{1-4}$ alkyl, G is hydrogen, $C_{1-4}$ alkyl, alkylphenyl wherein said phenyl group is optionally substituted by hydroxy or methylenedioxy, or is alkylamino, ii)

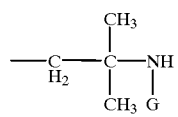

wherein G is as defined above, iii)

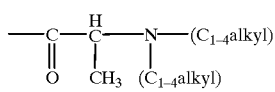

iv)

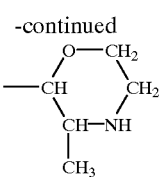

v)

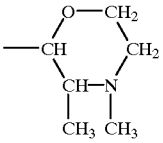

b)

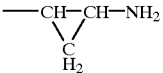

c)

—CH$_2$CH$_2$NH—NH$_2$    and d)

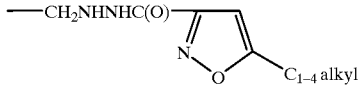

each $R_4$ is independently selected from hydrogen, hydroxyl, sulfhydryl, alkyl, aryl, alkoxy, mercaptoalkyl, aryloxy, mercaptoaryl, alkaryloxy, mercaptoalkaryl, nitro, amino, N-alkylamino, N-arylamino, N-alkarylamino, fluoro, chloro, bromo, iodo and trifluoromethyl, $R_5$ is selected from the group consisting of hydroxyl, sulfhydryl, alkyl, aryl, alkoxy, mercaptoalkyl, aryloxy, mercaptoaryl, alkaryloxy, mercaptoalkaryl, nitro, amino, N-alkylamino, N-arylamino, fluoro, chloro, bromo, iodo and trifluoromethyl, $R_6$ is hydrogen, halo, trifluoromethyl or alkyl of 1 to 4 carbon atoms, $R_7$ is selected from the same groups as $R_4$ or may be hydroxyalkyl or 1–2 carbon atoms, $R_8$ is hydrogen or hydroxymethyl, $R_9$ is hydrogen or alkyl of 1 to 6 carbon atoms, or $R_2$ and $R_9$ may jointly form a keto group provided that $R_1$ is hydroxy or amino, X is oxygen or NH, and Y is nitrogen with the proviso that when X is O, $R_3$ is not methyl when $R_1$ is methoxy, $R_2$ is hydroxy, all $R_4$'s are hydrogen or a pharmaceutically acceptable acid addition salt thereof.

Preferably the aryl groups are phenyl or naphthyl or in the case of $R^2$ when this is a carbamate group, 1-naphthyl groups, the aryloxy groups are phenoxy groups, the aralkyl groups are benzyl groups and the aralkyloxy groups are benzyloxy groups.

Preferred compounds include those wherein $R^1$ and $R^2$ are each selected from H,   OR,   SH,   NH$_2$   or   NHR,

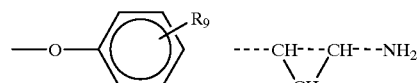

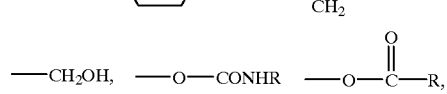

-continued

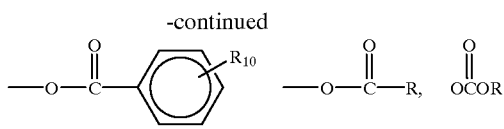

wherein R is alkyl 1–6 carbon atoms, phenyl or naphthyl $R^5$-substituted phenyl naphthyl or benzyl wherein $R_{10}$ is hydrogen, alkyl or alkoxy, $R^3$ is —H, or branched on linear lower alkyl or

wherein n is 3, 4 or 5 or

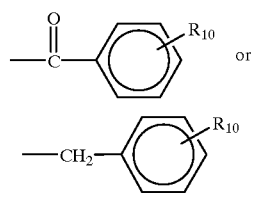

wherein $R_{10}$ is as defined above.

Preferred $R_3$ groups are normally electron-donating such as lower alkyl groups such methyl and tertiary butyl and phenyl and substituted phenyl groups such as hydroxy phenyl, p-alkoxy phenyl, p-amino phenyl and p-alkyl phenyl. However, groups such as benzyl and benzoyl may also be of use.

X is preferably oxygen and Y is nitrogen.

When used herein the term "lower alkyl" means alkyl of 1–6 carbon atoms, preferably 1–4 carbon atoms, most commonly methyl or ethyl.

Compounds likely to be of particular use are those wherein $R_3$ is hydrogen, lower alkyl or cyclopropyl methyl and $R_1$ and $R_2$ are each independently hydroxy, lower alkoxy, lower alkanoyl or benzoyl or carbamate groups and the analogous dihydro compounds wherein the cyclohexene ring of galanthamine is saturated. Thus, $R_1$ may typically be hydroxy, methoxy, ethoxy or carbamoyl of the formula $CONHR_{11}$ wherein $R_{11}$ is methyl, ethyl, n-propyl, n-butyl, n-valeroyl, phenyl, naphthyl or fluoro or nitro substituted phenyl or naphthyl, $R_2$ may typically be hydroxy, methoxy, ethoxy, acetyloxy, propionoyloxy, n-valeroyloxy, i-valeroyloxy, or $CONHR_{11}$ wherein $R_{11}$ is as defined above. $R_3$ is typically hydrogen, methyl or ethyl.

Particularly preferred compounds include childanthine, lycoramine, galanthamine esters and galanthamine—and O-desmethyl galanthamine carbamates and the corresponding N-desmethyl compounds. The galanthamine and O-desmethyl galanthamine carbamates are believed to be novel compounds.

One class of compounds according to the present invention are those of the formula:

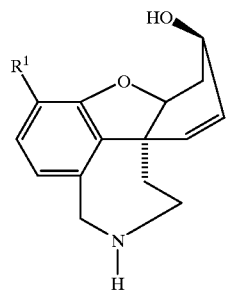

wherein $R^1$ is as defined above, preferably hydroxy, lower alkoxy, aryloxy, substituted aryloxy, benzyloxy or $R^5$ substituted benzyloxy, amino, alkyl amino or an alkyl or aryl carbamyl group.

For example, such compounds include O-desmethyl, N-desmethylgalanthamine; O-ethyl, O-desmethyl, N-desmethylgalanthamine; O-phenyl, O-desmethyl, N-desmethylgalanthamine; and O-benzyl, O-desmethyl, N-desmethylgalanthamine. Useful carbamates may include phenylcarbamyl O-desmethyl, N-desmethylgalanthamine; mono α-naphthylcarbamyl O-desmethyl N-desmethyl galanthamine and dimethylcarbamyl O-desmethyl, N-desmethylgalanthamine.

A second class are those of the formula:

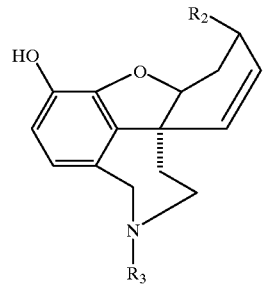

wherein $R^2$ is hydroxy, lower alkoxy, aryloxy, mono or di alkyl or aryl carbamates $R^5$ substituted aryloxy benzyloxy or $R^5$ substituted benzyloxy or an alkyl or aryl carbamyl group and $R^3$ is hydrogen or alkyl of 1–6 carbon atoms such as methyl ethyl, methyl cyclopropyl, benzyl or benzoyl or $R^5$-substituted benzyl or benzoyl. Suitable $R_3$ groups are as described above. Such Compounds include O-desmethylgalanthamine; chlidanthine; O-desmethylgalanthamine-2-O-methyl ether; O-desmethylgalanthamine-2-O-ethyl ether; O-desmethylgalanthamine-2-O-benzyl ether; O-desmethylgalanthamine-2-O-phenyl ether and O-desmethyl-N-desmethylgalanthamine-2-naphthyl carbamate; O-desmethylgalanthamine-2 (lower alkyl) carbamates such as n-butyl carbamate; O-desmethylgalanthamine-2-dimethyl carbamate and O-desmethylgalanthamine-2-diethyl carbamate wherein the carbamyl group is bonded to the oxygen of the cyclohexene ring, and the corresponding N-desmethyl and N-desmethyl N-ethyl and N-desmethyl N-cyclopropyl methyl and N-desmethyl N-benzyl compounds.

O-Desmethyl-N-desmethyl-N-ethyl galanthamine; O-desmethyl-N-desmethyl-N-ethyl galanthamine-O-methyl, O-ethyl or O-benzyl ether wherein said etherification is in the 2-position; O-desmethyl-N-desmethyl-N-ethylgalanthamine phenyl, α-naphthyl, dimethyl or diethyl carbamate wherein said carbamate substitution is in the 2-position; O-desmethyl-N-desmethyl-N-cyclopropylmethylgalanthamine O-methyl, O-ethyl or O-benzyl ether wherein said etherification is in the 2-position; O-desmethyl-N-desmethyl-N-cyclopropylmethylgalanthamine; O-desmethyl-N-desmethyl-N-cyclopropylmethylgalanthamine O-methyl, O-ethyl or O-benzyl ether wherein said etherification is in the 2-position; O-desmethyl-N-desmethyl-N-cyclopropylmethyl galanthamine phenyl, α-naphthyl, dimethyl or diethyl carbamate wherein said carbamate substitution is in the 2-position; O-desmethyl-N-desmethyl-N-benzylgalanthamine; O-desmethyl-N-desmethyl-N-benzylgalanthamine O-methyl, O-ethyl or O-benzyl ether wherein said etherification is in the 2-position, O-desmethyl-N-desmethyl-N-benzylgalanthamine phenyl, α-naphthyl, dimethyl or diethyl carbamate wherein the carbamate substitution is in the 2-position.

A third class of compounds comprises those of the formula:

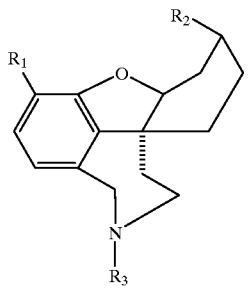

wherein $R^1$, $R^2$ and $R^3$ are as defined above, $R^1$ typically being hydroxy, amino lower alkoxy, benzyloxy or $R^5$ substituted benzyloxy, amino alkylamino or alkyl or aryl carbamyl, $R^2$ is hydroxy, lower alkoxy, aryloxy, benzyloxy or an alkyl or aryl carbamyl group but is preferably hydroxy and $R^3$ is typically hydrogen, methyl, ethyl, cyclopropylmethyl, phenyl, p-hydroxy phenyl, p-aminophenyl, p-alkoxyphenyl or p-alkylphenyl or benzyl.

Such compounds include, for example, O-desmethyllycoramine; N-desmethyl-O-desmethyllycoramine; N-desmethyl-N-ethyl lycoramine; N-desmethyl-N-cyclopropylmethyllycoramine; N-desmethyl-N-benzyllycoramine; O-desmethyllycoramine ethyl ether; deoxy-O-desmethyllycoramine; O-deoxy-N-desmethyllycoramine.

A further class comprising compounds of the formula:

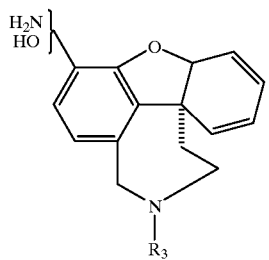

wherein $R^3$ is selected from hydrogen, lower alkyl, cycloalkyl methyl or benzyl;

A further class of compounds are narwedine derivatives where $R_1$ is hydroxy and $R_3$ as defined above, typically hydrogen, lower alkyl, cycloalkyl methyl or benzyl. Such compounds many contain $R_4$ and $R_5$ substituents as noted above.

Compounds of the above formula I where $R_2$ is hydroxyl and $R_4$ is a moiety of formula I wherein $R_1$ is hydrogen and $R_2$ is a linking bond are compounds in which the structure of formula I has linked at ring position 2 a hydroxyl group and a second formula I structure wherein $R_2$ is a bond linking the second formula I structure to said position 2 of the first and in said second formula I structure, $R_2$ is hydrogen. Such compounds may be made by reacting a compound of formula I wherein $R_2$ is hydroxyl to convert the hydroxyl to a halide, reacting the halide to form a Grignard compound, and reacting the latter with a galanthamine ketone.

Useful compounds may include the following:

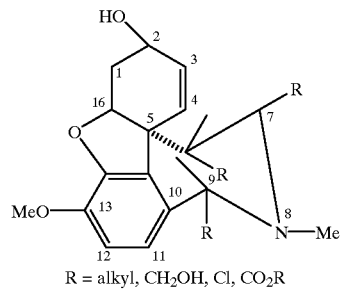

R = alkyl, CH$_2$OH, Cl, CO$_2$R

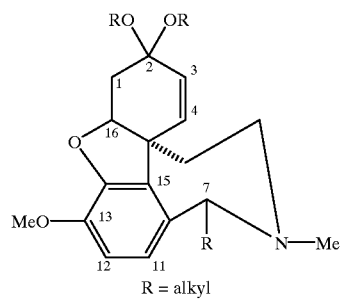

R = alkyl

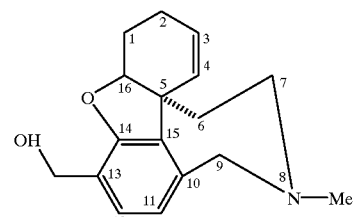

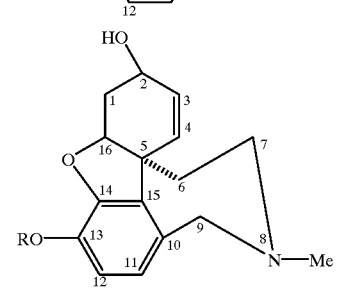

R = CONMe$_2$
R = CH$_2$COOH

-continued

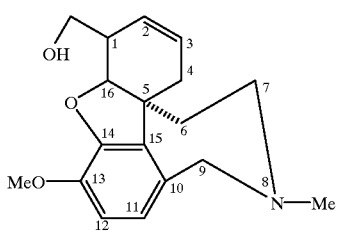

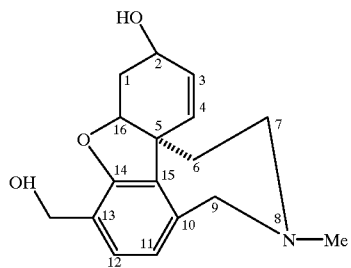

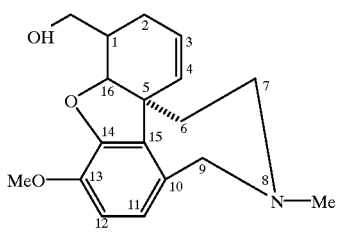

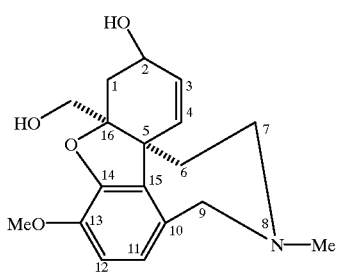

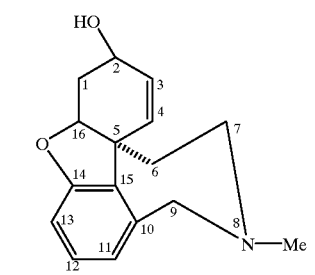

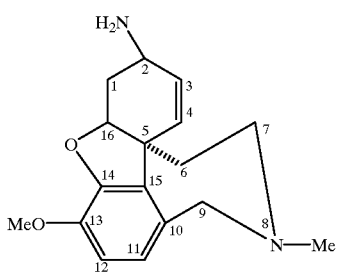

-continued

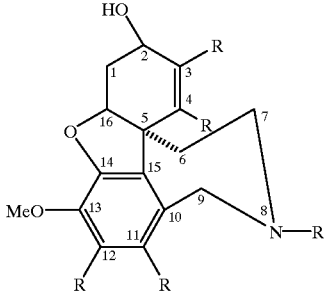

R = alkyl groups

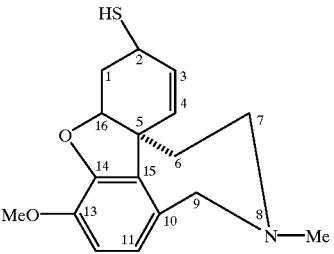

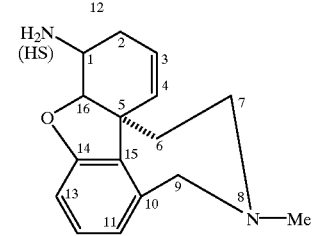

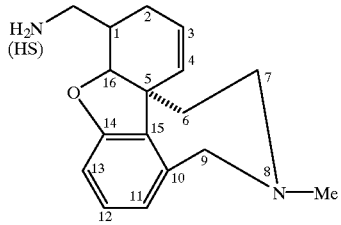

The novel compounds of the present invention in addition to their use for treatment of Alzheimer's disease can find use in a variety of other circumstances where cholinesterase inhibition is desired.

Many compounds of the present invention may be obtained by effecting suitable conversions of galanthamine. Galanthamine has the structure:

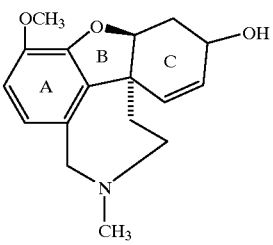

Compounds wherein $R_1$ is other than methoxy can be obtained from galanthamine by demethylation to the corresponding phenol and, if desired, effecting subsequent conversion thereon. Demethylation may be effected with iodotrimethylsilane in accordance with the method described by M. E. Jung and M. A. Lyster in J. Org. Chem. 42 3761 (1977). Reaction with iodotrimethylsilane may be effected in any convenient solvent, for example, chloroform at moderate temperatures (typically 25–40° C.) for several hours (e.g. 12–20 hours) to cleave the methyl group.

The phenol obtained by this reaction may be employed itself or used as an intermediate for the production of other active compounds. If it is desired to avoid effecting the same reactions at the allylic hydroxy group in the C ring as are to take place at the phenol group, that is produced by demethylation of the A ring, it is desirable to protect the allylic hydroxyl group when carrying out further interconversions. Suitable protection can be effected by converting the allylic hydroxyl group to its tetrahydropyranyl ether or 4-methoxytetra-hydropyranyl ether. Such ethers can be formed by reaction with dihydropyran or 4-methoxytetrahydropyran in a solvent such as dichloromethane at room temperature, and in the presence of a strong organic acid such as p-toluenesulfonic acid. When desired, the protective groups can be removed, the tetrahydropyranyl group, for example, by treatment with methanol and Dowex-50 WX8 and the 4-methoxytetrahydropyranyl group by reaction with very dilute (e.g., 0.01N) hydrochloric acid.

The phenolic group obtained by demethylation of the methoxy group of galanthamine may readily be converted into an alkali metal salt by reaction with sodium or potassium hydroxide or reaction with sodium hydride in tetrahydrofuran. The salt so obtained may be "alkylated" by reaction with an appropriate alkyl, aryl, alkaryl or $R_5$-substituted aryl or alkaryl or heterocyclic or $R_5$-substituted heterocyclic halide to produce a compound wherein $R_1$ is alkoxy (other than methoxy), aryloxy, alkaryloxy, $R_5$-substituted aryloxy, $R_5$-substituted alkoxy or heterocyclic or $R_5$-substituted heterocyclic. The reaction with the halide is typically run with excess halide in the absence of solvent or in a solvent such as dimethyl formamide or dimethylsulfoxide. For less reactive halides, the presence of a silver oxide catalyst may be desirable.

Reaction of the phenolic group with an isocyanate can be used to introduce a monoalkyl or monoaryl carbamyl group.

Dialkyl or diaryl carbamates may be obtained [by] from the mono alkyl or aryl carbamates by reaction with sodium hydride and an alkyl or aryl iodide. For example, the dimethyl carbamate can be obtained by reaction of the hydroxy group with methyl isocyanate followed by reaction with sodium hydride and methyl iodide.

Conversion of the phenolic group to an amino group, which can subsequently be alkylated by conventional means to produce a secondary amine if desired, can be effected by the Bucherer reaction using sodium bisulfite and ammonia.

The phenol group may be esterified, for example, with an acid anhydride or acid halide to produce an alkanoyloxy or aralkanoyloxy, $R_1$ group.

Production of compounds wherein $R_1$ is sulfhydryl or an alkyl-, aryl-, aralkylthio group can be effected by first converting the phenolic hydroxyl group obtained by demethylation of galanthamine to a thiol group. This can be effected, for example, by the Newman-Kwart rearrangement described, for example, in S. Patai ed "The Chemistry of the Thiol Group" Part 1 John Wiley & Sons, New York 1974 pages 201–206. This rearrangement is effected in three steps:

(1) conversion of the hydroxyl group to the O-aryl dialkylthiocarbamate by treatment with dialkylthiocarbonyl chloride;

(2) pyrolysis of the O-aryl dialkylthio-carbamate to the S-aryl dialkylthiocarbamate; and (3) hydrolysis of this product to the aryl mercaptan.

The first stage reaction with dimethylthio-carbamyl chloride may be effected by dissolving the phenol obtained by demethylation of galanthamine in aqueous potassium hydroxide at 10° C. or below and then reacting this with dimethylthiocarbamyl chloride in tetrahydrofuran at temperatures not exceeding 12° C. The solution is made alkaline and the O-aryl dimethyl-thiocarbamate is separated. This compound is pyrolyzed at 270–275° C. for about 45 minutes in a salt bath, and treated with potassium hydroxide in ethylene glycol. The reaction is cooled, the product extracted and worked up.

The thiol group can be converted to an alkali metal salt if desired by reaction with sodium or potassium hydroxide or sodium hydride. This salt may be alkylated to produce compounds wherein $R_1$ is alkylthio, arylthio, aralkylthio or alkarylthio by any one of a wide variety of alkylating agents, for example, as described by P. D. Boyer in J. Amer. Chem. Soc., 76:4331 (1954).

The production of the thiol group also provides a convenient route for the production of compounds wherein $R_1$ is hydrogen. The thiol may be desulfurized, for example, by refluxing with Raney nickel in absolute alcohol or dioxane, for example, as described by R. L. Augustine "Catalytic Hydrogenation" Marcel Dekker Inc., New York 1965 pp 131–133.

Production of a galanthamine analogue where $R_2$ is an alkanoyloxy or benzoyl group can be obtained by a simple esterification reaction. Compounds wherein $R_2$ is alkyloxy, aryloxy, aralkyloxy or alkaryloxy may be formed by forming a salt of the alcohol by reaction with sodium and thereafter reacting the salt with alkyl or other halide as described above for alkylating a phenol salt to produce $R_1$ as other than methyl.

Similarly, reaction of the hydroxy group with an aryl or alkyl isocyanate will produce compounds wherein $R_2$ is a monoaryl or monoalkyl carbamate.

In other transformations of the $R_2$ group, the first step in modification will normally be conversion of the allylic alcohol in-so an allylic bromide by reaction with bromine or an alkyl bromide. This may be effected by reaction with a slight excess of carbon tetrachloride and triphenylphosphine in a solvent such as methylene chloride at reduced temperature, for example, around 0° C. The bromide may then be reacted with magnesium in a Grignard reaction and the Grignard reagent obtained reacted with water to produce a compound wherein $R_2$ is hydrogen. Alternatively, reaction of the allylic bromide with lithium aluminum hydride may achieve the same product.

The allyl bromide may also be used as an intermediate for the introduction of other groups into the C ring. For example, the bromide will react with nucleophiles such as sodium or potassium hydrosulfide to replace the bromo group by a hydrosulfuryl group or with sodium cyanide to introduce a cyano group. The hydrosulfuryl group may be converted into a salt and alkylated in the same ways as can a hydrosulfuryl group in the A ring.

The allylic hydroxyl group may also be converted into a keto group. This can be accomplished, for example, by reaction with Jones reagent ($H_2CrO_4$, $H_2SO_4$ water and acetone). Proceeding via the keto group may also be an alternative route to production of compounds wherein $R_2$ is hydrogen. For example, the keto compound may be reacted with ethane dithiol and boron trifluoride etherate and the 1,3-dithiolane produced then desulfurized by reaction with Raney nickel.

The ketone intermediate may also be used as a source for compounds wherein $R_2$ is amino, such compounds being obtained by reductive amination of the keto group with ammonia and hydrogen in the presence of a nickel catalyst.

Further analogues that can be obtained by use of the ketone as an intermediate are those wherein $R_9$ is other than hydrogen. These can be obtained by reaction of the ketone with a Grignard reagent.

The ketone may also be used as an intermediate for the production of compounds wherein $R_7$ is hydroxy methyl by first effecting an α-bromination of the ketone and then converting this to hydroxy methyl.

When $R_2$ and $R_9$ jointly form a semicarbazone this can be formed from the ketone by reaction with semicarbazide.

The corresponding oxime and phenylcarbazones may also be obtained from the keto compound by reaction with hydroxylamine and phenylhydrazine respectively.

In order to produce compounds wherein $R_3$ is other than methyl, galanthamine is first demethylated to produce a compound wherein $R_3$ is hydrogen. Demethylation may be effected by reaction with a chloroformate such as methyl chloroformate or phenyl chloroformate to produce a carbamate which may then be cleaved with hydrazine, or by reaction with β, β, β-trichloromethyl chloroformate followed by reaction with zinc and acetic acid. In an alternative N-demethylation route, the hydroxy group is first protected by acetylation and the acetyl ester then reacted with 1-chloroethyl chloroformate in a halogenated solvent to replace the N-methyl group by a—$COOCHClCH_3$ group which may itself be removed by heating in methanol. The resulting amine may then be alkylated with other alkyl groups, branched or unbranched, alkylphenyl group or alkylheterocyclic groups. This reaction may be carried out by converting —NH to the corresponding sodium or potassium salt (NaH, KH) and treating the salt with the corresponding halide, preferably iodides, but bromides and chlorides might be used. All the halides used are commercially available. The reaction conditions may be modified for less reactive halides such as chlorides or aryl or heterocyclic halides which may also be less reactive. For instance, a special method is needed for N-phenylation as described by D. H. R. Barton, J. P. Finet and J. Khamsi, Tetrahedron Lett., 28:887 (1987).

A chlorine atom may be introduced to the cyclohexenol ring of galanthamine by reaction with an acid chloride of a strong organic sulfonic acid such as p-toluene sulfonyl chloride. This reaction proceeding with simultaneous elimination of the hydroxyl group to produce:

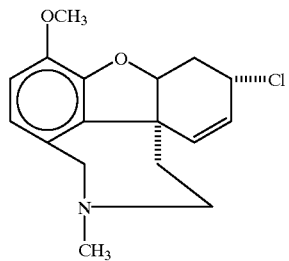

which may itself be used as an intermediate to react with nucleophiles such as alkoxides, azides and cyanides to introduce such groups into the ring at the 2 or 4 positions.

It is also possible to change the degree of saturation of the "core" structure of galanthamine. For example, if one forms an allylic bromide in the C-ring as described above, this bromide may be subject to catalytic hydrogenation in the presence of palladium, for example, palladium on carbon in ethanol at room temperature and atmospheric pressure to remove not only the bromine atom, but also to saturate the unsaturated bond in the C ring.

The C-ring may be oxidized to produce a further unsaturated bond by oxidation, for example, by heating with nickel, platinum or palladium at 300–350° C. or possibly under milder conditions if acceptors such as maleic acid, cyclohexene or benzene are present.

The oxygen of the B ring of galanthamine may be replaced by N—R' by reaction with ammonia or an amine in the gas phase at high temperatures in the presence of activated aluminum oxide or aluminum silicate as described, for example, in Yu. K. Yur'ev and E. G. Vendel'shtein, Zh. Obshch. Khim., 21: 259 (1951); Chem. Abstr., 45:7564 (1951); Ibid. 23, 2053 (1953); Chem. Abstr., 49: 3120 (1955); H. Sugisawa and K. Aso, Tohoku J. Agr. Res., 10: 137 (1959); Chem. Abstr., 54: 11015 (1960).

$R^6$ substituents may be introduced into the D-ring for example by Procedure No. 4 hereinafter.

Conversion of $R_8$ to hydroxy methyl may be effected by photolysis in the presence of cyanogen chloride to introduce a cyano group. This may be reduced using a Raney rickel catalyst to produce an aldehyde group that can itself be reduced to hydroxy methyl.

Similar conversions can be effected using lycoramine as starting material to produce compounds wherein the C ring is saturated.

In addition to modifying galanthamine, compounds according to the present invention may also be produced by cyclizing an amide of the formula:

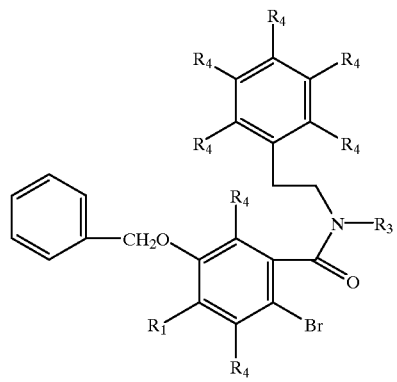

$R_1$, $R_3$ and $R_4$ groups may be selected as desired in the starting material employed. Cyclization is effected by electrochemical oxidation of the type described in U.S. Pat. No. 4,290,862 for preparing narwedine-type enones. The linear precursor in an appropriate solvent with a conductive salt and 2% $HBF_4$ or $KClO_4$ or $K_2CO_3$ is added to the anode compartment of an electrolytic cell. The cathode compartment and the electrolytic bridge of the reference electrode contains the same anodic solvent and the same percentage of conductive salt. The working electrode is platinum. Oxidation is carried out at 1.3 volts at low temperatures (below 0° C.). This procedures after workup of the product affords cyclization products.

Choice of a suitably substituted starting material permits the production of final products where the $R_4$ groups are other than hydrogen.

PROCEDURES

1. Conversion of Oxygen to Nitrogen in Furanoid Ring

This transformation has been accomplished by several authors. Passage of furan and its homologs, or reduced furans with ammonia over alumina, a; 400–4500° C., affords the corresponding pyrroles. With primary, amines the N-substituted pyrrole is obtained. A typical procedure is as follows. The furan derivative is dissolved in liquid ammonia and passed over an alumina catalyst (200 c.c. 4–6 mesh) which has been preheated to 400° C.[1] Alternatively, a mixture of a furan derivative and ammonia in aqueous-alcoholic medium may be heated at temperature around 110–150° C. The reaction proceeds more readily under pressure and therefore can be carried out in an autoclave.[2]

1. C. L. Wilson, J. Chem. Soc., 63, (1945).
2. R. C. Fuson, C. L. Fleming, R. Johnson, J. Am. Chem. Soc. 60: 1994 (1938).

2. Introduction of —CH₂OH at Position 16

Position 16 is next to the furan ring. This position is equivalent to the α-position of an ether and therefore prone to radical attack by reagents such as oxygen, peroxides, and photochemical reactions.

Irradiation of cyclic ethers in the presence of cyanogen 3.chloride is known to produce a-cyano ethers in good yields.[1] Therefore, a similar reaction on galanthamine should introduce a cyano group in this position. The cyano group is known to be converted to an aldehyde with Raney Nickel and formic acid.[2] The aldehyde may in turn be reduced with any reducing agents to the hydroxymethyl group.[3]

1. E. Muller, H. Huber, Chem. Ber. 96, 2319 (1963).
2. T. van Es, B. Stakun, J. Chem. Soc. 5775 (1965).
3. S. R. Sandler, W. Karo, "Organic Functional Group Preparations", Vol. 12, 1968. Academic Press, pp. 89–90.

A typical procedure is as follows. The photolysis is carried out using a mercury lamp S-81 in a water cooled, unfiltered quartz immersion well. A solution of equimolar amounts of galanthamine and cyanogen chloride, in a spectral grade solvent, is irradiated with stirring, in a nitrogen atmosphere, and in a quartz cell. The reaction is irradiated for 2 h in the presence of sodium bicarbonate. The sodium bicarbonate is essential to absorb the hydrogen chloride. Lower yields are obtained in the absence of the reagent.

The final mixture is filtered, concentrated, washed with appropriate reagents and dried. Removal of solvent affords the product.

The cyano derivative obtained is dissolved in 75% (v/v) of aqueous formic acid and treated with a 50:50 Ni—Al alloy (Raney type). The mixture is heated for 3 h at 95° C., diluted with absolute ethanol-ethyl acetate and filtered through Celite. The filtrate is concentrated, washed with appropriated reagents and dried. Removal of solvent affords the product.

The aldehyde derivative is dissolved in isopropanol and added to a solution of sodium hydroxide and sodium borohydride, dropwise, at such rate that the reaction refluxes gently. After standing overnight, the reaction is worked up as usual.

3. Conversion of —OMe at Position 13 to Other Substituents

The reaction will require demethylation of the methoxy group. Although demethylation of aromatic alkoxy group is considered a standard reaction, this operation may be tricky in polysubstituted systems. A successful approach is the reaction of boron tribromide at 0° C.[1] The phenol obtained may be converted to a bromide by standard procedure.[2] Generation of a lithium anion at this position[3] allows a variety of reactions such as treatment with alkyl halides to give alkyl groups, carbon dioxide to afford acids or aldehydes and ketones to give alcohols.

1. S -Y Han, J. T. Gordon, K. Bhat, M. B. Dratman, M. M. Joullie', Int. J. Peptide Protein Res., 30:652 (1987).
2. C. E. Kaslow and M. M. Marsh, J. Org. Chem., 12: 456 (1947).
3. J. Chiarello and M. M. Joullie', Tetrahedron, 44:41 (1988).

A typical procedure follows. A 1M solution of boron tribromide is added dropwise to a solution of galanthamine in dry methylene chloride at 0° C., under nitrogen. After stirring at 0° C. for 3 h, the excess reagent and boron complexes are hydrolyzed by water. The product is obtained by extraction of the aqueous layer with ether. Removal of the solvent affords the compound.

The phenol derivative is mixed thoroughly with phosphorous pentabromide and heated at 70–80° C., then at 120° C. Hydrolysis with ice and water affords the crude bromo compound which may be recrystallized from an appropriate solvent.

A solution of n-butyl lithium was added dropwise, at –78° C., under argon, to the bromo derivative dissolved in tetrahydrofuran and hexamethylphosphoramide to generate the intermediate anion.

To this anion, one may add any alkyl halide to form the corresponding derivative. Alternatively, the solution could be poured over dry ice to afford the corresponding carboxylic acid, or to an aldehyde or ketone to form the corresponding alcohol derivative.

Treatment of this anion with ethyl chloracetate would give the corresponding ethyl carboxymethyl derivative. The above methodology is general to introduce various groups in place of the methoxy group in the aromatic ring (position 13).

4. Conversions in the D ring

Removal of the methyl group in the D ring of galanthamine can be accomplished by the classical von Braun reaction.[1] The reaction may be manipulated to give either demethylation to a secondary amine or to open the ring. Either of these procedures will give rise to new analogs. Ring opening would afford two chains, one at position 10, possibly a bromoethyl groups and one at position 5, a N-methylpropylamine. These could be used to study the effect of disrupting ring D.

1. H. A. Hagerman, Org. Reactions, VII, Chap 4 (1953).

However, demethylation would serve to introduce functionality in ring D via the formation of an imine. A typical procedure for introduction of substituents in ring D follows. Treatment of N-demethylated galanthamine with tert-butyl hypochlorite at 0° C. will afford the N-chloro derivative. This sensitive compound is not isolated but immediately dehalogenated with either sodium methoxide or diazabicycloundecene to afford the highly unstable pyrroline. This intermediate can be treated with nucleophiles[3] or with benzoic acid and, tert-butylisonitrile as described in reference 2.

2. R. F. Nutt, M. M. Joullie', J. Am. Chem., Soc., 104, 5852(1982).
3. J. Hausler, U. Schmidt, Liebigs Ann. Chem. 1881 (1979).

The compounds of the present invention may be used for the treatment of Alzheimer's disease either in free base form or as the acid addition salts.

The compounds can be administered in any convenient chemical or physical form. For example, they may be administered as pharmaceutically acceptable salts, as long as these do not quaternize the D-ring nitrogen atom. Useful salts include the hydrobromide and hydrochloride.

The compounds or the pharmaceutically-acceptable acid addition salts may be administered to a patient suffering from Alzheimer's disease orally or by subcutaneous or intravenous or injection. Sustained release delivery mechanisms are particularly useful for administration of the compounds of the present invention, for example, intracerebroventricularly by means of an implanted reservoir by use of sustained release capsules or by means of a trans dermal patch. It may be necessary to begin at lower doses than are ultimately effective.

Certain of the compounds may be only sparingly soluble in water at room temperature and so injectable compositions are normally in the form of an aqueous suspension. If necessary, pharmaceutically-acceptable suspension aids may be employed. Typically, such a suspension will be employed at a concentration of 1–50 mg/ml more commonly 5–40 mg/ml, for example, 5–30 mg/ml or 10–40 mg/ml, typically 20–30 mg/ml of the compound of the present invention. Typical dosage rates when administering compounds of the invention will depend upon the exact nature and condition of the patient. For example, typical dosage rates for administration by injection are in the range 5–1,000 mg per day depending upon the patient. In some cases, even lower dosages such as 0.5 or 1 mg per day may be helpful. For example, divided doses in the range 0.5–5 mg/kg body weight per day may prove useful. Typically, one might administer a dosage of 50–300 mg per day to a patient of a body weight of 40–100 kg, although in appropriate cases such dosages may prove useful for patients having a body weight outside this range. In other cases, dosages as low as 0.1 mg and as high as 500 mg may be appropriate for persons in this body weight range.

The compounds of the invention may also be administered orally, for example, as an aqueous suspension or a solution in aqueous ethanol or as a solid such as a tablet or capsule. Suspensions or solutions for oral administration are typically of about the same concentration as those used for injections. However, it may be desirable when administering the drug orally to use a higher dosage rate than when administering it by injection. For example, dosages up to 200 mg per day may be used, such as dosages in the range 10–60 mg per day. In preparing such tablets or capsules, standard tablet or capsule-making techniques may be employed. The dosage rate of the compound of the invention or its pharmaceutically-acceptable salt will normally be in the same range as for oral administration of a liquid. If desired, a pharmaceutically-acceptable carrier such as starch or lactose may be used in preparing tablets. Capsules may be prepared using soft gelatine as the encapsulating agent. If desired, such capsules may be in the form of sustained release capsules wherein the main capsule contains microcapsules of active compound which release the contents over a period of several hours thereby maintaining a constant level of active compound in the patient's blood stream.

The following test provides a good animal model for Alzheimer's disease in humans: A selective lesion is placed in a subcortical nucleus (nucleus basalis of Meynert) with a resultant cortical cholinergic deficiency, similar in magnitude to that seen in early to moderate stage Alzheimer's disease. Numerous behavioral deficits, including the inability to learn and retain new information, characterizes this lesion. Drugs that can normalize these abnormalities would have a reasonable expectation of efficacy in Alzheimer's disease. Haroutunian, V, Kanof P. Davis, K L: Pharmacological alleviations of cholinergic-lesion-induced memory defects in rats. Life Sciences, 37:945–952 (1985).

The following specific formulations may find use in treatment of Alzheimer's disease:

Tablets or capsules containing 0.1, 0.5, 1.0, 5, 10 and 25 mg hydrobromide of a compound according to the invention to be taken four times a day, or a sustained-release-preparation delivering an equivalent daily dose.

Parenteral solution containing 5 mg/ml.

Liquid formulation for oral administration available in 5 mg/5 ml and 25 mg/5 ml concentration.

There have been reports that galanthamine can cause cardiac arrythmias. If such problems occur with the compounds of the present invention, it may be desirable to administer compounds of the invention in conjunction with another drug such as propantheline bromide to control such arrythmias. As with other drugs that act on the central nervous system, minor side effects, such as nausea, may be noted. In this case, the compounds of the present invention will be administered in conjunction with an agent for control of such side effects.

A substantial proportion of patients suffering from Alzheimer's disease exhibit not only reduced levels of acetyl choline but also of norepinephrine in the brain. In such cases, the compounds of the present invention may advantageously be employed in conjunction with compounds such as clonidine desipramine, monoamine oxidase inhibitors, methamphetamine and methyl phenidate that stimulate the noradrenergic receptors in the brain.

The production of compounds of the present invention is illustrated by the following Examples:

EXAMPLE 1

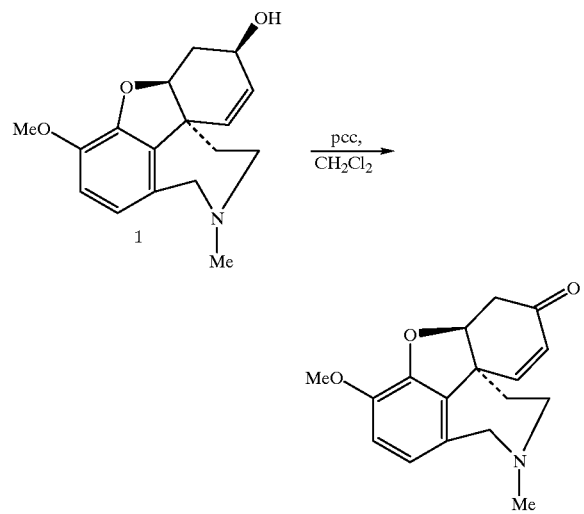

To a solution of galanthamine (1, 0.7 g, 0.2439 mmoles) in dry methylene chloride (4 ml), pyridinium chlorochromate (0.15779, 0.7317 moles) was added and stirred at room temperature for 8 hours. The reaction mixture was diluted with methanol and filtered. Removal of solvent followed by purification on a silica gel column using acetone, methanol:acetone (10:90) as eluants afforded the desired product. (0.06g, 86% yield). mp. 184–186° C.

EXAMPLE 2

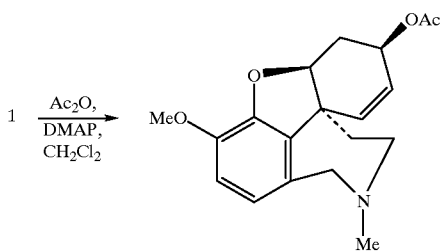

To a solution of 1 (0.07 g, 0.2439 mmoles) in methylene chloride, acetic anhydride (0.03 ml, 0 317 mmoles) and dimethylaminopyridine (0.0536g, 0.439 mmoles) were added at 0° C. in an ice bath. The reaction mixture was stirred at 0° C. for 10 minutes and room temperature for 60 minutes. Solvents were removed on a rotary evaporator and the residue was diluted with ethyl acetate, washed with water, 10% $Na_2CO_3$ solution, brine, and dried ($Na_2SO_4$). Concentration of the solvent and purification by silica gel chromatography first acetone, then MeOH:acetone (1:10) as eluants afforded 0.0773 g of product (96% yield).

mp. 126–128° C.

EXAMPLE 3

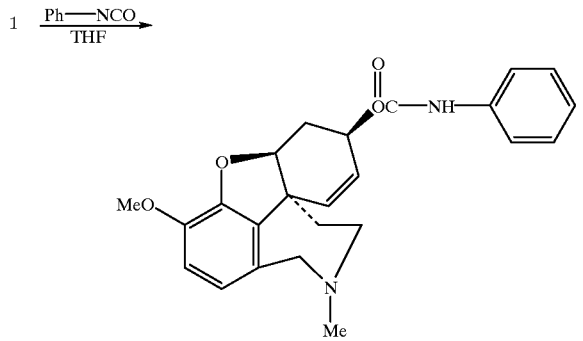

Phenylisocyanate (0.033 ml, 0.2926 mmoles) was added to a stirred solution of 1 (0.07 g, 0.2439 mmoles) in THF (5 ml) at room temperature, and then stirred for 30 hours under the same conditions. The reaction mixture was concentrated, purified by silica gel column chromatography using first acetone, then MeOH:acetone (10:90) to give 0.0982 g (99% yield) of product.

mp 79–81° C.

EXAMPLE 4

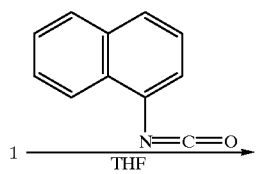

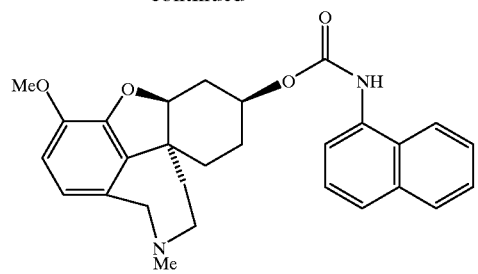

1-Naphthylisocyanate (0.042 ml, 0.2926 mmoles) was added to a stirred solution of 1 (0.07 g, 0.2439 mmoles) in THF (5 ml) at room temperature. The reaction mixture was stirred for 24 hours at room temperature, and then concentrated. The crude reaction mixture was purified by silica gel column chromatography using first acetone, then methanol:acetone (10:90) as eluants to afford 0.11 g of product (99%).

mp. 198–200° C.

EXAMPLE 5

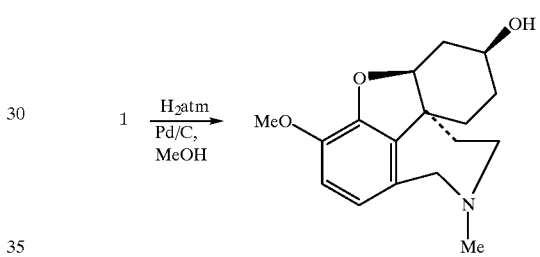

A solution of 1 (0.1 g, 0.3484 mmoles) in 2ml of dry methanol, and 20% palladium on carbon (0.02 g) was hydrogenated in a hydrogenator. The reaction mixture was shaken for 10 hours at room temperature. The catalyst was collected on Celite, and washed thoroughly with methanol. The solution was concentrated, and the crude material was purified on a silica gel column using acetone:methanol (90:10, 80:20) to afford 0.0938 g (93% yield) of the product.

mp 110–112° C.

The anticholinesterase activity of the compounds prepared in the above examples was assayed by an assay for inhibition of acetylcholinesterase following the procedure of G. Ellman, Biological Pharmacology, 7:88–95 (1961) Acetylthiocholine serves as substrate since it acts like acetylcholine. Acetylcholinesterase cleaves it to thiocholine and acetate which react with dithiobisnitrobenzoate to form a yellow color which is measured photometrically.

The assay results are shown in the following table, which also includes an assay of the activity of galanthamine.

This assay was carried out at dilution of $10^{-5}$ molar

TABLE

| COMPOUND | PERCENT INHIBITION OF ACETYLCHOLINESTERASE |
| --- | --- |
| Galanthamine | 95% |
| Product of Example 1 | 10% |
| Product of Example 2 | 37% |

TABLE-continued

| COMPOUND | PERCENT INHIBITION OF ACETYLCHOLINESTERASE |
| --- | --- |
| Product of Example 3 | 37% |
| Product of Example 4 | 60% |
| Product of Example 5 | 30% |

EXAMPLE 6

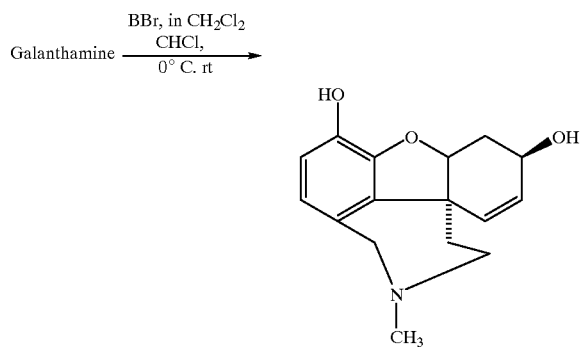

Galanthamine (0.3 g, 1.0452 mmol) was dissolved in CHCl$_3$ (20 ml), and the solution cooled to 0° C. in an ice bath. A 1M solution of BBr$_3$ in CH$_2$Cl$_2$ (6.2712 mmol, 6.3 ml) was added all at once. The reaction mixture was then warmed to room temperature and stirred for 8 hours. The resulting reaction mixture was poured into 20% solution of NH$_4$OH mixed with ice (v/v) and stirred for 0.5 hr. The resulting solution was separated, dried over Na$_2$SO$_4$, concentrated, and then purified by column chromatography using methanol:acetone (30:70) as eluant to give O-demethyl galanthamine in low yield.

EXAMPLE 7

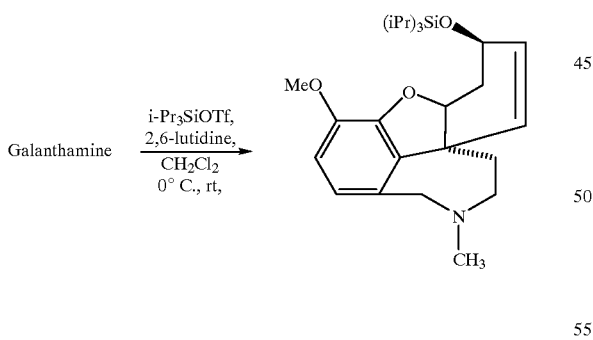

Galanthamine was dissolved in CH$_2$Cl$_2$ (4 ml), and the solution cooled to 0° C. in an ice bath. Triisopropylsilyl trifluoromethanesulfonate was added to the reaction mixture, followed by 2,6-lutidine, under an argon atmosphere. The reaction mixture was warmed to room temperature, stirred for one hour, and then diluted five times with ether, washed with 5% NaHCO$_3$, and then with saturated sodium chloride solution. The organic layer was dried over Na$_2$SO$_4$, concentrated, and purified by silica gel column chromatography, (acetone, acetone:methanol; 95:5) to give the product in quantitative yield as a yellow oil which was soluble in alcohols.

EXAMPLE 8

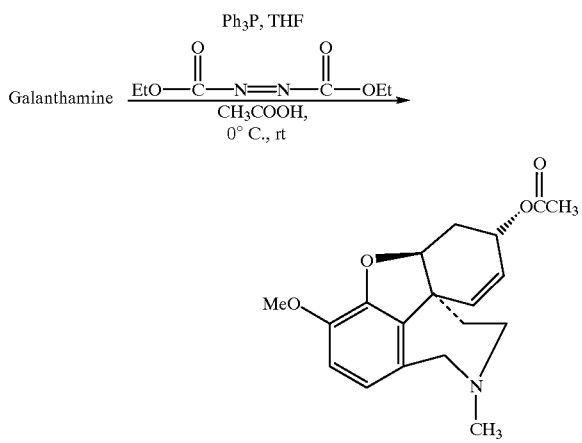

Galanthamine (0.12g, 0.4181 mmol) was dissolved in dry THF (5 ml), and the solution cooled to 0° C. in an ice bath. Ph$_3$P (0.1426 g, 0.5435 mmol) and diethylazodicarboxylate (0.1092 g, 0.1 ml, 0.6271 mmol) were added to the reaction mixture, followed by freshly distilled glacial acetic acid (0.0528 g, 0.06 ml, 0.878 mmol). The reaction mixture was warmed to room temperature, and stirred for 24 hours at the same condition. The resulting mixture was washed with 5% NaHCO$_3$ solution, and then saturated sodium chloride solution. The organic layer was dried over Na$_2$SO$_4$, concentrated, and then purified by silica gel column chromatography (acetone, and then acetone:methanol, 95:5) to give the product (0.069 g, 50% yield), which was soluble in alcohols.

EXAMPLE 9

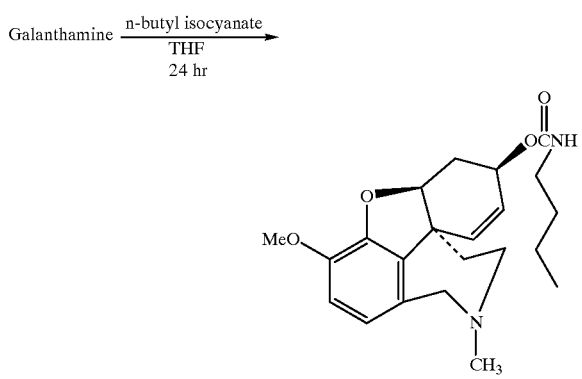

Galanthamine (0.1 g, 0.3484 mmol) was dissolved in 7 ml of dry THF. n-Butyl isocyanate (0.0691 g, 0.08 ml, 0.6968 mmol) was added to the reaction mixture at room temperature, under an argon atmosphere. The reaction mixture was refluxed for 20 hours. The solvent was concentrated, and then purified by silica gel column chromatography using first acetone, and then acetone:methanol (19:1) to give the product in quantitative yield as a white foam, which was soluble in alcohols.

EXAMPLE 10

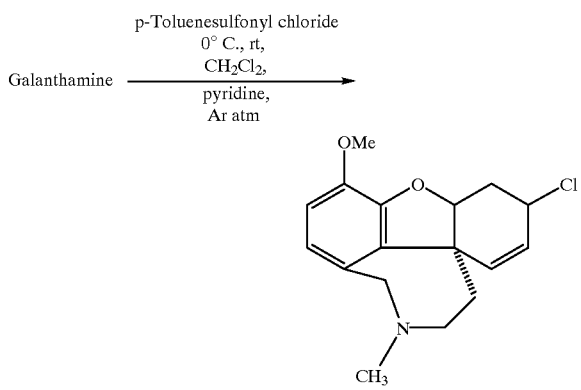

Galanthamine (0.1427 g, 0.4972 mmol) was dissolved in CH$_2$Cl$_2$ (5 ml), and the solution cooled to 2° C. To the solution was added para-toluenesulfonyl choride (0.2274 g, 1.1932 mmol) and pyridine (0.7866 g, 9.944 mmol, 0.8 ml). The reaction mixture was stirred for 12 hours at room temperature, under an argon atmosphere. The reaction mixture was then diluted with methylene chloride and saturated sodium chloride aqueous solution, filtered, separated. The resulting organic layer was washed with brine, dried over Na$_2$SO$_4$, concentrated, purified by silica gel column chromatography with acetone as an eluant to afford the product (0.0733 g, 48% yield).

EXAMPLE 11

3[(Aminocarbonyl)hydrozono]3-deoxygalanthamine

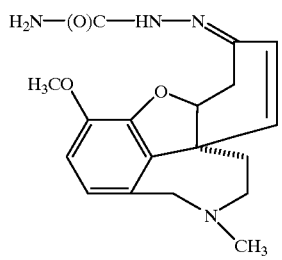

3[(Aminocarbonyl)hydrozono]3-deoxygalanthamine (0.079 g, 0.2 mmol) was dissolved in 3 ml of ethanol, and H$_2$O (1 ml) was added. Semicarbazide hydrochloride (0.0587 g, 0.5262 mmol) and sodium acetate (0.0863 g, 1.0524 mmol) were added to the reaction mixture. The reaction mixture was warmed to 100° C. and stirred for 5 hours. It was then concentrated in vacuo to remove the alcohol. The aqueous reaction solution was allowed to cool to crystallize the product. The crystals of semicarbazone were removed by filtration and recrystallized from methanol and diethyl ether to afford 0.061 g (64% yield) of narwedine semicarbazone as white crystals, mp 264° C. (decomposition).

The product was soluble in alcohols

EXAMPLE 12

Galanthamine Methiodide

Galanthamine (0.25 g, 0.871 mmol) was dissolved in dry diethyl ether (50 ml), and methyl iodide (0.1854 g, 1.3065 mmol, 0.081 mmol) was added. The reaction mixture was stirred for 5 hours at room temperature under an argon atmosphere. The white solid which formed was collected, washed with ether and then recrystallized from hot water and methanol to afford white crystals, up 289–291. The product was soluble in hot water and slightly soluble in cold water. The yield of galanthamine methiodide was 0.2904 g (78%).

EXAMPLE 13

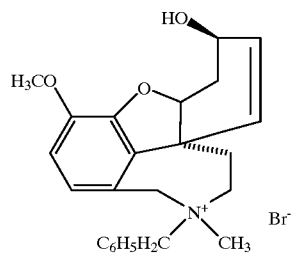

Galanthamine (1, 0.25 g, 0.871 mmol) was dissolved in 50 ml of dry ether. Benzyl bromide (0.2235 g, 0.16 ml, 1.3065 mmol) was added, and the reaction mixture was stirred for 20 hours at room temperature, under an argon atmosphere. The white precipitate formed was collected and thoroughly washed with ether. The crystals were recrystallized from methanol and ether to give galanthamine benzyl bromide (0.3272 g, 82% yield) as white crystals. mp 192° C. (decomposition)

The product was soluble in alcohols.

The compounds were tested in the assay described after Example 5 but at different concentrations. The results obtained were as follows:

|  | Concentration | | |
|---|---|---|---|
|  | $10^{-5}$ | $10^{-6}$ molar | $10^{-9}$ molar |
| galanthamine | 93 | 68 | 22 |
| O-demethyl-galanthamine | 100+ | 89 | 55 |
| galanthamine benzyl bromide | — | 77 | 40 |
| galanthamine methiodidie | 97 | 75 | 29 |
| N-demethyl galanthamine | 88 | 56 | 15 |
| galanthamine n-butyl carbamate | 75 |  |  |
| Product of Example 10 | 73 |  |  |
| epigalanthamine acetate (from Example 8) | 21 |  |  |
| Product of Example 7 | 17 |  |  |
| narwedine semicarbazone | inactive |  |  |
| N-demethyl lycoramine | inactive |  |  |

Further compounds were prepared by methods analogous to those described above and were tested in a cholinesterase assay as described above. The results were as follows as cholinesterase inhibition at $10^{-5}$ M:

| | |
|---|---|
| N-allyl galanthamine bromide | 96 |
| lycoramine azide | 25 |
| lycoramine | 30 |
| 4,5-dehydrogalanthamine | 30 |
| 2-amino-2-dehydroxy lycoramine | 17 |
| 2-iodo-2-dehydroxy lycoramine | 15 |

Other cholinesterase activity tests for compounds according to the invention produced the following results, which may, however, be less reliable than those noted above.

Acetylcholinesterase Inhibition Assay

| Name | Structure ($R_1 = CH_3$) | % Inhibition at $10^{-5}$ | $10^{-6}$ | $10^{-7}$ |
|---|---|---|---|---|
| Galanthamine | $R_2 = H$<br>$R_3 = CH_3$ | 93 | 52 | 13 |
| n-butyl carbamate | $R_2 = CONHnBu$<br>$R_3 = CH_3$ | 44 | 37 | 9 |
| n-propyl carbamate | $R_2 = CONHnPr$<br>$R_3 = CH_3$ | 34 | 50 | 21 |
| propyl ester | $R_2 = OCOCH_3$<br>$R_3 = CH_3$ | 51 | 48 | 40 |
| ethyl carbamate | $R_2 = CONHEt$<br>$R_3 = CH_3$ | 59 | 70 | 9 |
| o-F-benzoic ester | $R_2 = $ O-fluoro-benzoic<br>$R_3 = CH_3$ | 27 | 39 | 37 |
| o-F-phenoxypropionic ester | $R_2 = OCO(CH_2)_2O$-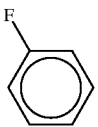<br>$R_3 = CH_3$ | 17 | 15 | 0 |
| 3-NO$_2$-4-F-phenyl carbamate | $R_2 = OCONH$-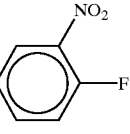<br>$R_3 = CH_3$ | 48 | 51 | 64 |
| iso-valeroyl ester | $R_2 = OCOCH_2CH(CH_3)_2$<br>$R_3 = CH_3$ | 33 | 39 | 13 |
| valeric ester | $R_2 = OCO(CH_2)_3CH_3$<br>$R_3 = CH_3$ | 41 | 35 | 37 |
| hexanoic ester | $R_2 = OCO(CH_2)_4CH_3$<br>$R_3 = CH_3$ | 55 | 30 | 36 |
| decanoic ester | $R_2 = OCO(CH_2)_6CH_3$<br>$R_3 = CH_3$ | 30 | 24 | 6 |
| octyl carbamate | $R_2 = OCONH(CH_2)_7CH_3$<br>$R_3 = CH_3$ | 55 | 35 | 16 |
| imide | $R_2 = $<br>$R_3 = CH_3$ | 10 | 29 | 12 |
| cyclopropyl carbinol ester | $R_2 = OCO$—cyclopropyl<br>$R_3 = CH_3$ | 40 | 13 | 0 |
| isopropyl carbamate | $R_2 = OCONHCH$—$(CH_3)_2$<br>$R_3 = CH_3$ | 21 | 0 | 0 |

Acetyl cholinesterase inhibition data was also obtained for a compound wherein the methoxy group of galanthamine was replaced by an N-methyl carbamate group and for childanthine. In this case, IC$_{50}$ data was obtained and compared with that for galanthamine

| | S | |
|---|---|---|
| | 5 mM | 0.3 mM |
| O-demethyl-galanthamine-13-methyl carbamate | 0.002 | 0.002 |
| childanthine | 0.31 | 0.08 |
| galanthamine | 9.7 | 0.7 |

In vivo Testing

Galanthamine n-butyl carbamate was tested in the nucleus basalis model for galanthamine discussed in the Hartounian et al paper noted above. In the test, mice were given the drug three and ½ hours before two learning trials in a shuttle box.

They are placed in the lighted compartment and receive an electric footshock when they cross into the preferred side, the dark. The next day, they are again placed in the lighted compartment and the time to enter the dark is noted. The latency to enter the dark compartment is the basis for this figure. In this passive avoidance test, results were obtained with the n-butyl carbamate that were comparable with those obtained with galanthamine but that the best dose with the n-butyl carbamate was 0.5 mg/kg whereas with galanthamine the best dose was 3 mg/kg. Two mice given 100 mg/kg of the n-butyl carbamate showed cholinergic side effects but neither died. Below 50 mg/kg no side effects were noted.

In a similar test using normal mice, the mice remained in the light (less preferred) side of the shuttle box for over six minutes at the best dose (0.1 mg/kg) as compared to a best dose result of about 90 seconds for the nucleas basalis-lesioned animals.

In a second set of test chosen to mimic certain aspects of Alzheimer's disease, a scopolamine dementia dark avoidance test, three galanthamine analogs were evaluated for their ability to antagonize a scopolamine induced memory deficit in a passive avoidance paradigm in mice. Furnished data on the effects of these compound on cholinesterase activity were used to determine doses for testing. N-Demethyl galanthamine was inactive in antagonizing the scopolamine induced memory deficit at doses of 0.3, 1.0 and 3.0 mg/kg sc. The two other compounds were tested at 1, 3 and 10 mg/kg sc and did antagonize the scopolamine induced deficit. Galanthamine acetate was active at doses of 3 and 10 mg/kg sc; lycoramine was active at 10 mg/kg sc.

Training and testing of passive avoidance were conducted in a two-compartment (light/dark) test cage. On the training day, mice were individually placed in the light half of the cage and after entering the dark compartment, were administered a 3 sec 0.4 mA footshock. They were then removed from the test chamber and returned to their home cages. Twenty-four hours later, the animals were again placed in the lighted half of the test cage and the latency to enter the dark compartment was measured.

All animals in each group of 15 naive male CFW mice were injected twice subcutaneously. Thirty minutes prior to training, animals were administered 3 mg/kg scopolamine HBr or its 0.9% NaCl vehicle. Five minutes prior to training, independent groups were administered one of three doses of the test compounds or the distilled water vehicle. One group in each experiment received vehicle twice, another group received scopolamine and the dH$_2$O vehicle; the remaining groups received scopolamine and a test compound.

A cutoff value (CO), defined as the second-longest latency in the scopolamine/vehicle treated group, was used to determine whether a compound was active. If 20% or more of the animals in a treatment group had latencies greater than the CO value, the compound was considered active at that dose.

Results

The three compounds were tested in two separate experiments; the results are presented below in Tables 1 and 2. Doses considered active are marked with an asterisk (*).

TABLE 1

N-Demethylgalanthamine

| Treatment | Dose mg/kg sc | Mean Latency | # > CO/n | % > CO |
|---|---|---|---|---|
| saline | | 205 | 12/15 | |
| scopolamine | | 34 | | |
| scopolamine + | 0.3 | 21 | 0/15 | 0 |
| N-demethyl | 2.0 | 33 | 2/15 | 13 |
| galanthamine | 3.0 | 26 | 2/15 | 13 |

Cut-off value = 38 seconds

TABLE 2

Galanthamine Acetate and Lycoramine

| Treatment | Dose mg/kg sc | Mean Latency | # > CO/n | % > CO |
|---|---|---|---|---|
| saline | | 205 | 14/15 | |
| scopolamine | | 21 | | |
| scopolamine + | 1 | 21 | 1/15 | 7 |
| galanthamine | 3 | 38 | 4/15 | 27* |
| acetate | 10 | 31 | 3/15 | 20* |
| Scopolamine + | 1 | 26 | 1/15 | 7 |
| lycoramine | 3 | 19 | 0/15 | 0 |
| | 10 | 48 | 4/15 | 27* |

Cut-off value = 41 seconds

O-Demethyl galanthamine-13-methyl carbamate and childanthine were also tested in the same way. The carbamate showed activity at doses of 0.001–0.003 and childanthine at doses of 0.3. Lycoramine was also found to be active in this test.

A number of compounds were also evaluated in a standardized Profile of Observable Effects (POE) which involves administering drug to animals in increasing amounts and observing this for up to two hours to see wheter peripheral cholinergic effects such as tremor, lacrimation, salivation, pilo erection, defection or red eye occur. With subcutaneous administration to mice, such effects were no noted in any of four mice when using O-demethyl-galanthamine-13-methylcarbamate at a dosage of 0.31 mg/kg, were noticeable in one mouse out of four at 0.63 mg/kg and in all four mice at 1 mg/kg when using childanthine there were no noticeable effects in four mice at 20 mg/kg but noticeable effects in all four at 40 mg/kg (by way of comparison POE values for galanthamine were two out of four nice showing effects at 10 mg/kg but none showing effects at 5 mg/kg.

What is claimed is:

1. A method of inhibiting acetyl cholinesterase activity in a patient which comprises administering to said patient a therapeutically effective amount of a compound of the formula

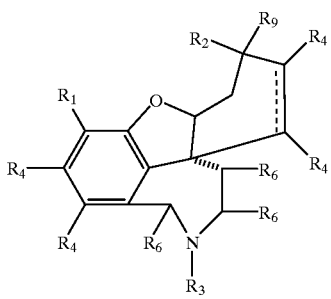

wherein the broken line represents an optionally present double bond, $R_1$ and $R_2$ are each selected independently from the group consisting of hydrogen, hydroxy, amino, alkylamino, cyano, sulfhydryl, alkoxy of 1–6 carbon atoms, aryloxy, aralkoxy, $R_5$-substituted aryloxy, monoalkyl, dialkyl or aryl carbamate group, wherein the monoalkyl, dialkyl or aryl moiety may be $R_5$-substituted or unsubstituted, ($R_5$-substituted aryl)oxymethyl, alkanoyloxy, hydroxy-substituted alkanoyloxy, benzoyloxy, and $R_5$-substituted benzoyloxy;

$R_3$ is hydrogen, straight or branched chain alkyl of 1–6 carbon atoms, cycloalkylmethyl, or alkylphenyl or $R_3$ is a heterocyclic selected from α- or β-furyl, or α- or β-thienyl, thenyl, pyridyl, pyrazinyl or pyrimidyl;

each $R_4$ is independently selected from the group consisting of hydrogen, hydroxyl, sulfhydryl, alkyl, aryl, alkoxy, aryloxy, alkaryloxy, nitro, amino, N-alkylamino, N-arylamino, N-alkarylamino, fluoro, chloro, bromo, iodo and trifluoromethyl;

$R_5$ is selected from the group consisting of hydroxyl, sulfhydryl, alkyl, aryl, alkoxy, aryloxy, alkaryloxy, nitro, amino, N-alkylamino, N-arylamino, N-alkarylamino, fluoro, chloro, bromo, iodo and trifluoromethyl;

$R_6$ is selected from the group consisting of hydrogen, halo, trifluoromethyl or alkyl of from 1 to 4 carbon atoms; $R_9$ is hydrogen or alkyl of 1 to 6 carbon atoms; or a pharmaceutically acceptable acid addition salt thereof with the proviso that $R_3$ is not methyl when $R_1$ is methoxy, $R_2$ is hydroxy and all $R_4$'s are hydrogen.

2. A method of inhibiting acetylcholinesterase activity in a patient which comprises administering to said patient a therapeutically effective amount of a compound of the formula:

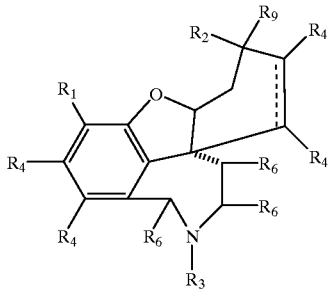

wherein the broken line represents an optionally present double bond; $R_1$ and $R_2$ are each selected independently from the group consisting of hydrogen, hydroxyl, amino, alkylamino, cyano, sulfhydryl, alkoxy of 1–6 carbon atoms, aryloxy, aralkoxy, $R_5$-substituted aryloxy, monoalkyl, dialkyl or aryl carbamate group, wherein the monoalkyl, dialkyl or aryl moiety may be $R_5$-substituted or unsubstituted, ($R_5$-substituted aryl)oxymethyl, alkanoyloxy, hydroxy-substituted alkanoyloxy, or benzoyloxy; $R_1$ may also be alkyl of up to 14 carbon atoms or hydroxymethyl;

$R_3$ is a residue of a compound having adrenergic or monoamine oxidase activity and said residue being selected from the group consisting of a)

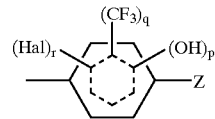

wherein Hal is a halogen, p is 0, 1 or 2, q is 0 or 1, r is 0 or 1 and Z is selected from the group consisting of i)

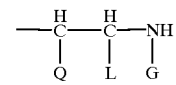

wherein Q is hydrogen or hydroxy, L is hydrogen or $C_{1-4}$ alkyl, G is hydrogen, $C_{1-4}$ alkyl, alkylphenyl wherein said phenyl group is optionally substituted by hydroxy, methylenedioxy or is alkylamino, ii)

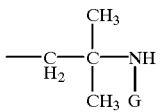

wherein G is as defined above, iii)

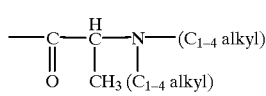

iv)

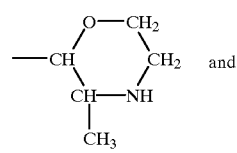

and v)

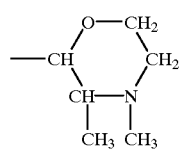

b)

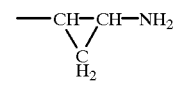

c)

——CH₂CH₂NH——NH₂ and d)

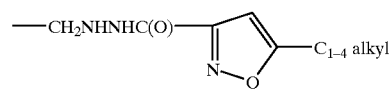

each R₄ group is independently selected from hydrogen, hydroxyl, alkyl, alkoxy, fluoro, chloro, bromo, iodo and trifluoromethyl;

R₅ is selected from the group consisting of hydroxyl, sulfhydryl, alkyl, aryl, alkoxy, aryloxy, alkaryloxy, nitro, amino, N-alkylamino, N-arylamino, fluoro, chloro, bromo, iodo and trifluoromethyl;

R₆ is hydrogen, halo, trifluoromethyl or alkyl of 1 to 4 carbon atoms and R₉ is hydrogen or alkyl of 1 to 6 carbon atoms or a pharmaceutically acceptable acid addition salt thereof.

3. A method of inhibiting acetyl cholinesterase activity in a patient which comprises administering to said patient a therapeutically effective amount of a compound selected from the group consisting of galanthamine-13-acetate and galanthamine monoalkyl, dialkyl or aryl carbamates.

4. A method according to claim 1 wherein said compound is of the formula

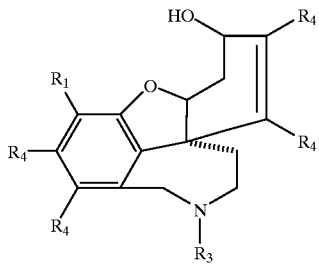

wherein R₁ is hydroxy, alkoxy of 1 to 6 carbon atoms, aryloxy, R₅-substituted aryloxy, benzoyloxy, R₅-substituted benzoyloxy, amino, alkylamino, or a monoalkyl, dialkyl or aryl carbamate group, wherein R₅ is selected from the group consisting of hydroxyl, sulfhydryl, alkyl, aryl, alkoxy, aryloxy, alkaryloxy, nitro, amino, N-alkylamino, N-arylamino, N-alkarylamino, fluoro, chloro, bromo, iodo, and trifluoromethyl; R₃ is hydrogen, straight or branched chain alkyl of 1–6 carbon atoms, cycloalkylmethyl or methylphenyl, and each R₄ is hydrogen.

5. A method of inhibiting acetylcholinesterase activity in a patient which comprises administering to said patient a therapeutically effective amount of a compound of the formula

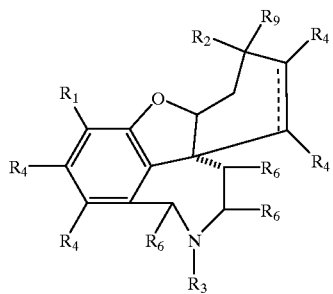

wherein R₁ is selected from the group consisting of hydroxy, methoxy, ethoxy, monoalkyl carbamate, dialkyl carbamate, phenyl carbamate, naphthyl carbamate, R₅-substituted phenyl carbamate and R₅-substituted naphthyl carbamate wherein R₅ is hydroxyl, sulfhydryl, alkyl, aryl, alkoxy, aryloxy, alkaryloxy, nitro, amino, N-alkylamino, N-arylamino, fluoro, chloro, bromo, iodo and trifluoromethyl, R₂ is selected from the group consisting of hydrogen, hydroxy, amino, alkylamino, cyano, sulfhydryl, alkoxy of 1–6 carbon atoms, aryloxy, aralkoxy, R₅-substituted aryloxy, monoalkyl, dialkyl or aryl carbamate group, wherein the monoalkyl, dialkyl or aryl moiety may be R₅-substituted or unsubstituted, (R₅-substituted aryl) oxymethyl, alkanoyloxy, hydroxy-substituted alkanoyloxy, benzoyloxy, and R₅-substituted benzoyloxy;

R₃ is hydrogen, straight or branched chain alkyl of 1–6 carbon atoms, cycloalkylmethyl, or alkylphenyl or R₃ is a heterocyclic selected from α- or β-thienyl, thenyl, pyridyl, pyrazinyl or pyrimidyl;

each R₄ is independently selected from the group consisting of hydrogen, hydroxyl, sulfhydryl, alkyl, aryl, alkoxy, aryloxy, alkaryloxy, nitro, amino, N-alkylamino, N-arylamino, N-alkarylamino, fluoro, chloro, bromo, iodo and trifluoromethyl;

R₅ is selected from the group consisting of hydroxyl, sulfhydryl, alkyl, aryl, alkoxy, aryloxy, alkaryloxy, nitro, amino, N-alkylamino, N-arylamino, N-alkarylamino, fluoro, chloro, bromo, iodo and trifluoromethyl;

R₆ is selected from the group consisting of hydrogen, halo, trifluoromethyl or alkyl of from 1 to 4 carbon atoms;

R₉ is hydrogen or alkyl of 1 to 6 carbon atoms; or a pharmaceutically acceptable acid addition salt thereof with the proviso that R₃ is not methyl when R₁ is methoxy, R₂ is hydroxy and all R₄'s are hydrogen.

6. A method of inhibiting acetylcholinesterase activity in a patient which comprises administering to said patient a therapeutically effective amount of a compound selected from O-desmethyl-N-desmethylgalanthamine; 13-O-ethyl-O-desmethyl-N-desmethylgalanthamine; 13-O-phenyl-O-desmethyl-N-desmethylgalanthamine; O-desmethyl-N-desmethyl-N-ethylgalanthamine; O-desmethyl-N-desmethyl-N-ethylgalanthamine 13-O-ethyl and 13-O-benzyl ethers; O-desmethyl-N-desmethyl-N-ethylgalanthamine 13-phenyl, 13-α-naphthyl, 13-dimethyl and 13-diethyl carbamates; O-desmethyl-N-desmethyl-N-cyclopropylmethylgalanthamine; N-desmethyl-N-cyclopropylmethylgalanthamine; O-desmethyl-N-desmethyl-N-cyclopropylmethylgalanthamine 13-O-ethyl and 13-O-benzyl ethers; O-desmethyl-N-desmethyl-cyclopropylmethylgalanthamine 13-phenyl, 13-α-naphthyl, 13-dimethyl and 13-diethyl carbamates; O-desmethyl-N-desmethyl-N-benzylgalanthamine; and O-desmethyl-N-desmethyl-N-benzylgalanthamine 13-O-methyl, 13-O-ethyl and 13-O-benzyl ethers.

7. A method of inhibiting acetylcholinesterase activity in a patient which comprises administering to said patient a therapeutically effective amount of a compound of the formula:

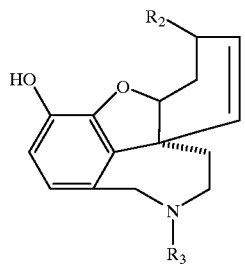

wherein R₂ is hydroxy, alkoxy of 1 to 6 atoms, aryloxy, R₅-substituted aryloxy, benzoyloxy or is a monoalkyl, dialkyl or aryl carbamate group, wherein the monoalkyl, dialkyl or aryl moiety may be R₅-substituted or unsubstituted wherein R₅ is alkyl, aryl, alkoxy, aryloxy, alkaryloxy, nitro, amino, N-alkylamino, N-arylamino, fluoro, chloro, bromo, iodo or trifluoromethyl; and R₃ is hydrogen, straight or branched chain alkyl of 1–6 carbon atoms, cycloalkylmethyl or methylphenyl.

8. A method according to claim 7, wherein R₂ is selected from the group consisting of hydroxy, alkoxy of 1 to 6 carbon atoms, benzyloxy, monoalkyl carbamate, phenyl carbamate, naphthyl carbamate, R₅-substituted phenyl carbamate and R₅-substituted naphthyl carbamate.

9. A method according to claim 1 wherein R₃ is selected from the group consisting of hydrogen, methyl, ethyl and cyclopropylmethyl.

10. A method of inhibiting acetylcholinesterase activity in a patient which comprises administering to said patient a therapeutically effective amount of a compound selected from the group consisting of O-desmethylgalanthamine; O-desmethylgalanthamine, O-methyl ether; O-desmethylgalanthamine, O-ethyl ether; O-desmethyl galanthamine, O-benzyl ether, wherein the etherification is at the 2-position; O-desmethylgalanthamine phenyl carbamate; O-desmethyl-N-desmethylgalanthamine α-naphthyl carbamate; O-desmethylgalanthamine dimethyl carbamate and O-desmethylgalanthamine diethyl carbamate wherein the carbamate group is bonded to the cyclohexene ring; O-desmethyl-N-desmethylgalanthamine; O-desmethyl-N-desmethylgalanthamine, O-methyl, O-ethyl and O-benzyl ethers wherein etherification is at the 2-position; O-desmethyl-N-desmethylgalanthamine, phenyl, α-naphthyl, dimethyl and diethyl carbamates wherein the carbamate substitution is at the 2-position; O-desmethyl-N-desmethyl-N-ethylgalanthamine; O-desmethyl-N-desmethyl-N-ethylgalanthamine, O-methyl, O-ethyl or O-benzyl ether wherein said etherification is in the 2-position; O-desmethyl-N-desmethyl-N-ethylgalanthamine phenyl, α-naphthyl, dimethyl or diethyl carbamate wherein said carbamate substitution is in the 2-position; O-desmethyl-N-desmethyl-N-cyclopropylmethylgalanthamine O-methyl, O-ethyl or O-benzyl ether wherein said etherification is in the 2-position; O-desmethyl-N-desmethyl-N-cyclopropylmethyl galanthamine; O-desmethyl-N-desmethyl-N-cyclopropylmethylgalanthamine phenyl, α-naphthyl, dimethyl or diethyl carbamate wherein said carbamate substitution is in the 2-position; O-desmethyl-N-desmethyl-N-benzyl galanthamine, O-methyl, O-ethyl or O-benzyl ether wherein said etherification is in the 2-position; and O-desmethyl-N-desmethyl-N-benzylgalanthamine phenyl, α-naphthyl, dimethyl or diethyl carbamate wherein the carbamate substitution is at the 2-position.

11. A method according to claim 1 wherein said compound is of the formula:

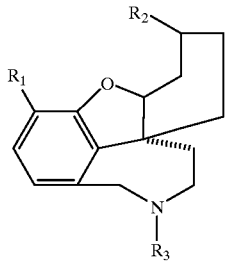

wherein R₁, R₂ and R₃ are as defined in claim 1.

12. A method according to claim 11 wherein R₁ is hydroxy, alkoxy of 1 to 6 carbon atoms, benzoyloxy, amino, alkylamino or monoalkyl, dialkyl, or aryl carbamate; R₂ is hydroxy, alkoxy of 1 to 6 carbon atoms, aryloxy, benzoyloxy or monoalkyl, dialkyl or aryl carbamate group and R₃ is hydrogen, methyl, ethyl, cyclopropylmethyl or alkylphenyl.

13. A method of inhibiting acetylcholinesterase activity in a patient which comprises administering to said patient a therapeutically effective amount of a compound selected from O-desmethyllycoramine; N-desmethyl-O-desmethyllycoramine; N-desmethyl-N-ethyllycoramine; N-desmethyl-N-benzyllycoramine; O-desmethyllycoramine ethyl ether; 2-deoxy-13-O-desmethyllycoramine; 2-O-deoxy-13-O-desmethyllycoramine benzyl ether; O-desmethyllycoramine dimethyl carbamate; O-desmethyllycoramine phenyl carbamate and 2-O-deoxy-13-desmethyllycoramine dimethyl carbamate.

14. A method according to claim 1, wherein said compound is administered orally in the form of a tablet or a capsule containing from 5, 10 or 25 mg of hydrobromide of said compound.

15. A method according to claim 4, wherein said compound is administered orally in the form of a tablet or a capsule containing from 5, 10 or 25 mg of hydrobromide of said compound.

16. A method according to claim 7, wherein said compound is administered orally in the form of a tablet or capsule containing from 5, 10 or 25 mg of hydrobromide of said compound.

17. A method according to claim 11, wherein said compound is administered orally in the form of a tablet or capsule containing from 5, 10 or 25 mg of hydrobromide of said compound.

18. A method according to claim 1, wherein a compound is administered in a sustained release formulation.

19. A method as claimed in claim 1 wherein the compound is one wherein R₁ is alkanoyloxy or a monoalkyl, dialkyl or aryl carbamate.

20. Galanthamine phenyl carbamate.

21. Galanthamine naphthyl carbamate.

22. A pharmaceutical composition comprising a compound of the formula:

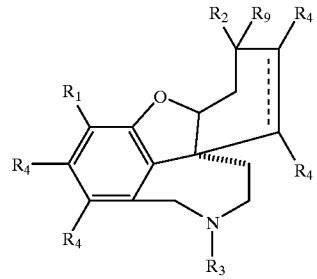

wherein the broken line represents an optionally present double bond, R₁ and R₂ are each selected independently from the group consisting of hydrogen, hydroxy, alkoxy of 1–6 carbon atoms, amino, alkylamino, cyano, sulfhydryl, or R₁ may be alkoxy of 1–6 carbon atoms provided that R₂ is not hydroxy, aryloxy, aralkoxy, R₅-substituted aryloxy, monoalkyl, dialkyl or aryl carbamate group, wherein the monoalkyl, dialkyl or aryl moiety may be R₅-substituted or unsubstituted, (R₅-substituted aryl)oxymethyl, alkanoyloxy, hydroxy-substituted alkanoyloxy, benzoyloxy, R₁ may also be alkyl of up to 14 carbon atoms, or hydroxymethyl;

R₃ is hydrogen, straight or branched chain alkyl of 1–6 carbon atoms, cycloalkylmethyl, alkylphenyl;

each R₄ is independently selected from the group consisting of hydrogen, hydroxyl, sulfhydryl, alkyl, aryl, alkoxy, aryloxy, alkaryloxy, nitro, amino, N-alkylamino, N-arylamino, N-alkarylamino, fluoro, chloro, bromo, iodo and trifluoromethyl;

$R_5$ is selected from the group consisting of hydroxyl, sulfhydryl, alkyl, aryl, alkoxy, aryloxy, alkaryloxy, nitro, amino, N-alkylamino, N-arylamino, fluoro, chloro, bromo, iodo and trifluoromethyl;

$R_9$ is hydrogen, or a pharmaceutically acceptable salt thereof and a pharmaceutically acceptable solvent, diluent or carrier with the provisos that 1) $R_1$ is not alkoxy of 1–6 carbon atoms, when $R_2$ is hydroxy, $R_3$ is methyl and all $R_4$'s are hydrogen;
2) $R_1$ is not acetoxy, when $R_2$ is hydroxy, $R_3$ is methyl and all $R_4$'s are hydrogen; or
3) the compound is not leucotamine, sanguinine or chlidanthine.

23. A composition according to claim 22 in the form of a sustained release product.

24. A composition according to claim 22 in the form of a tablet or capsule containing from 5, 10 or 25 mg of the hydrobromide of said compound.

25. A composition according to claim 22 wherein in said compound, $R_1$ and $R_2$ are each selected from the group consisting of hydrogen, alkanoyloxy, monoalkyl, dialkyl or aryl carbamates, wherein the monoalkyl, dialkyl or aryl moiety may be $R_5$-substituted, wherein $R_5$ is selected from the group consisting of hydrogen, hydroxyl, alkyl, aryl, alkoxy, aryloxy, alkaryloxy, nitro, fluoro, chloro, bromo, iodo and trifluoromethyl; $R_3$ is selected from the group consisting of alkyl, cycloalkylmethyl, and each $R_4$ is independently selected from the group consisting of hydrogen, hydroxyl, sulfhydryl, alkyl, aryl, alkoxy, aryloxy, alkaryloxy, nitro, amino, N-alkylamino, N-arylmino, fluoro, chloro, bromo, iodo and trifluoromethyl.

26. A composition as claimed in claim 25 wherein each $R_4$ is selected from the group consisting of hydrogen, fluoro, chloro, bromo, iodo and trifluoromethyl.

27. A composition as claimed in claim 25 wherein said compound is one wherein one of $R_1$ and $R_2$ is an alkanoyloxy.

28. A composition comprising a compound selected from the group consisting of galanthamine n-butyl carbamate, galanthamine phenyl carbamate, galanthamine naphthyl carbamate and galanthamine acetate or a pharmaceutically acceptable acid addition salt thereof and a pharmaceutically acceptable solvent, diluent or carrier.

29. A composition according to claim 22 wherein said compound is of the formula:

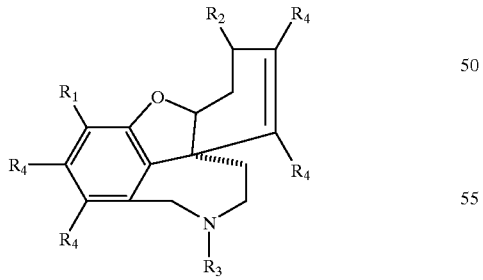

wherein $R_1$ and $R_2$ are each selected independently from the group consisting of hydrogen, hydroxy, amino, alkylamino, cyano, sulfhydryl, aryloxy, aralkoxy, $R_5$-substituted aryloxy, monoalkyl, dialkyl or aryl carbamate group, wherein the monoalkyl, dialkyl or aryl moiety may be $R_5$-substituted or unsubstituted, alkanoyloxy, hydroxy-substituted alkanoyloxy, and benzoyloxy, wherein $R_5$ is alkyl or alkoxy; $R_3$ is hydrogen, straight or branched chain alkyl of 1–6 carbon atoms, cycloalkylmethyl, or alkphenyl; with the provisos that 1) $R_1$ is not acetoxy when $R_2$ is hydroxy and $R_3$ is methyl and 2) that the compound is not leucotamine or sanguinine.

30. A composition according to claim 22 wherein said compound is of the formula:

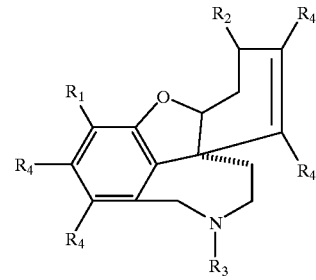

wherein $R_1$ is selected from the group consisting of hydrogen, hydroxy, amino, alkylamino, cyano, sulfhydryl, alkoxy of from 1 to 6 carbon atoms, aryloxy, aralkoxy, $R_5$-substituted aryloxy, monoalkyl, dialkyl or aryl carbamate group, wherein the monoalkyl, dialkyl or aryl moiety may be $R_5$-substituted or unsubstituted, ($R_5$-substituted aryl) oxymethyl, alkanoyloxy, hydroxy-substituted alkanoyloxy, or benzoyloxy, wherein $R_5$ is alkyl or alkoxy;

$R_2$ is selected from the group consisting of hydrogen, amino, alkylamino, cyano, sulfhydryl, alkoxy of from 1 to 6 carbon atoms, aryloxy, aralkoxy, or $R_5$-substituted phenyl or benzyl carbamate, $R_5$-substituted aryloxy, a monoalkyl, dialkyl or aryl carbamate group, ($R_5$ -substituted aryl)oxymethyl, alkanoyloxy, hydroxy-substituted alkanoyloxy, or benzoyloxy, wherein $R_5$ is alkyl or alkoxy;

$R_3$ is hydrogen, straight or branched chain alkyl of 1–6 atoms, cycloalkylmethyl, or alkylphenyl; each $R_4$ is independently selected from the group consisting of hydrogen, hydroxyl, sulfhydryl, alkyl, aryl, alkoxy, aryloxy, alkaryloxy, nitro, amino, N-alkylamino, N-alkarylamino, N-arylamino, fluoro, chloro, bromo, iodo and trifluoromethyl or a pharmaceutically acceptable salt thereof and a pharmaceutically acceptable solvent, diluent or carrier with the proviso that the compound is not leucotamine, O-methylleucotamine, O-methylleucotamine acetic acid ester, sanguinine or chlidanthine.

31. A composition according to claim 22 wherein said compound is of the formula

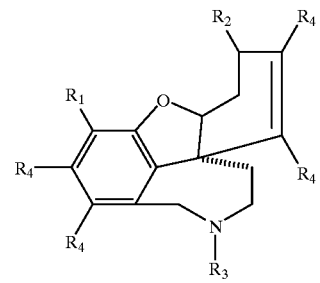

wherein $R_1$ is selected from the group consisting of hydrogen, hydroxy, amino, alkylamino, cyano, sulfhydryl, aryloxy, aralkoxy, $R_5$-substituted aryloxy, a monoalkyl, dialkyl, or aryl carbamate group wherein the monoalkyl, dialkyl or aryl moiety may be $R_5$-substituted or unsubstituted; ($R_5$-substituted aryl) oxymethyl, alkanoyloxy, hydroxy-substituted alkanoyloxy, or benzoyloxy, wherein $R_5$ is alkyl or alkoxy;

$R_2$ is selected from the group consisting of hydrogen, hydroxy, amino, alkylamino, cyano, sulfhydryl, alkoxy of from 1 to 6 carbon atoms, aryloxy, aralkoxy, or $R_5$-substituted phenyl or benzyl carbamate, $R_5$-substituted aryloxy, a monoalkyl, dialkyl or aryl carbamate group, ($R_5$-substituted aryl)oxymethyl, alkanoyloxy, hydroxy-substituted alkanoyloxy, or benzoyloxy, wherein $R_5$ is alkyl or alkoxy;

$R_3$ is hydrogen, straight or branched chain alkyl of 1–6 carbon atoms, cycloalkylmethyl, or alkylphenyl; each $R_4$ is independently selected from the group consisting of hydrogen, hydroxyl, alkyl, alkoxy, fluoro, chloro, bromo, iodo and trifluoromethyl or a pharmaceutically acceptable salt thereof and a pharmaceutically acceptable carrier, diluent or solvent with the proviso that the compound is not leucotamine, sanguinine, or chlidanthine.

32. A method of inhibiting acetylcholinesterase activity in a patient which comprises administering to said patient a therapeutically effective amount of a compound of the formula

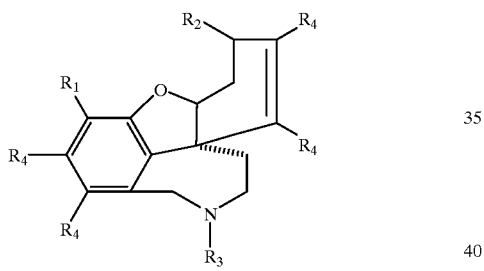

wherein $R_1$ and $R_2$ are each selected independently from the group consisting of hydroxy, amino, alkylamino, cyano, sulfhydryl, aryloxy, aralkoxy, $R_5$-substituted aryloxy, a monoalkyl, dialkyl or aryl carbamate group, $R_5$-substituted aryl)oxymethyl, alkanoyloxy, hydroxy-substituted alkanoyloxy, benzoyloxy, and $R_5$-substituted benzoyloxy, wherein $R_5$ is alkyl or alkoxy;

$R_3$ is hydrogen, straight or branched chain alkyl of 1–6 carbon atoms, cycloalkylmethyl, or alkylphenyl and all of $R_4$ are independently hydrogen, alkyl, alkoxy, fluoro, chloro, bromo, iodo, or trifluoromethyl or a pharmaceutically acceptable acid addition salt thereof and a pharmaceutically acceptable carrier diluent or solvent with the proviso that the compound is not leucotamine, or sanguinine.

33. A composition according to claim 22 wherein said compound is one wherein said broken line represents either no double bond or a single double bond in the 3,4 position, $R_1$ and $R_2$ are each selected from hydroxy, alkanoyloxy and monoalkyl, dialkyl or aryl carbamate; $R_3$ is selected from hydrogen, alkyl, cycloalkylmethyl and alkylphenyl and each of $R_4$ and $R_9$ is hydrogen.

34. A compound of the formula:

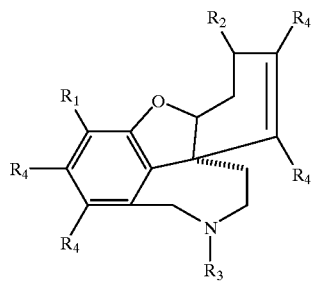

wherein $R_1$ is selected from the group consisting of hydrogen, amino, alkylamino, cyano, sulfhydryl, aryloxy, aralkoxy, $R_5$-substituted aryloxy, a monoalkyl, dialkyl or aryl carbamate group, wherein the monoalkyl, dialkyl or aryl moiety may be $R_5$-substituted or unsubstituted, ($R_5$-substituted aryl) oxymethyl, hydroxy-substituted alkanoyloxy, or benzoyloxy, wherein $R_5$ is alkyl or alkoxy;

$R_2$ is selected from the group consisting of hydrogen, hydroxy, amino, alkylamino, cyano, sulfhydryl, alkoxy of from 1 to 6 carbon atoms, aryloxy, aralkoxy, $R_5$-substituted aryloxy, a monoalkyl, dialkyl or aryl carbamate group, wherein the monoalkyl, dialkyl or aryl moiety may be $R_5$-substituted or unsubstituted, alkanoyloxy, hydroxy-substituted alkanoyloxy, or benzoyloxy, wherein $R_5$ is alkyl or alkoxy;

$R_3$ is hydrogen, straight or branched chain alkyl of 1–6 carbon atoms, cycloalkylmethyl, or alkylphenyl; each $R_4$ is independently selected from the group consisting of hydrogen, hydroxyl, alkyl, alkoxy, fluoro, chloro, bromo, iodo and trifluoromethyl or a pharmaceutically acceptable salt thereof provided that $R_2$ is not hydroxy when $R_1$ is hydrogen and $R_3$ is methyl and $R_4$ is hydrogen.

35. A compound of the formula

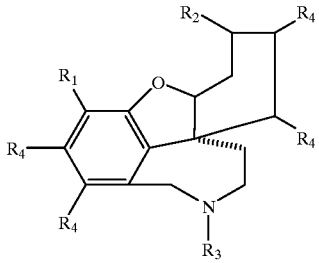

wherein $R_1$ is OCONHR wherein R is alkyl of 1–6 carbon atoms, phenyl, or $R_5$-substituted phenyl, or $R_5$-substituted benzyl wherein $R_5$ is selected from alkyl or alkoxy;

$R_2$ is hydroxy, alkoxy of 1–6 carbon atoms, alkanoyloxy, or OCONHR wherein R alkyl of 1–6 carbon atoms, phenyl, or $R_5$-substituted phenyl, wherein $R_5$ is selected from alkyl or alkoxy; $R_3$ is hydrogen, lower alkyl or cyclopropylmethyl and $R_4$ is hydrogen or a pharmaceutically acceptable salt thereof.

36. A method of inhibiting acetylcholinesterase activity in a patient which comprises administering to said patient a therapeutically effective amount of a compound selected from the group consisting of N-desmethyl-O-desmethyllycoramine; N-desmethyl-N-ethyllycoramine; N-benzyllycoramine; 2-O-deoxy-13-O-desmethyllycoramine benzyl ether; O-desmethyllycoramine dimethyl carbamate; O-desmethyllycoramine phenyl carbamate; and 2-O-deoxy-13-desmethyllycoramine dimethyl carbamate.

37. A compound of the formula

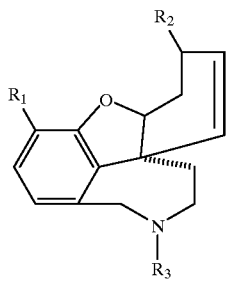

wherein $R_1$ is selected from the group consisting of hydrogen, hydroxy, amino, alkylamino, cyano, sulfhydryl, alkoxy of from 1 to 6 carbon atoms, aryloxy, aralkoxy, $R_5$-substituted aryloxy, a monoalkyl, dialkyl or aryl carbamate group, wherein the monoalkyl, dialkyl or aryl moiety may be $R_5$-substituted or unsubstituted, ($R_5$-substituted aryl) oxymethyl, alkanoyloxy, hydroxy-substituted alkanoyloxy, and benzoyloxy, wherein $R_5$ is alkyl or alkoxy;

$R_2$ is selected from the group consisting of hydrogen, amino, alkylamino, cyano, sulfhydryl, alkoxy of 1 to 6 carbon atoms, aryloxy, aralkoxy, $R_5$-substituted aryloxy, a monoalkyl, dialkyl or aryl carbamate, wherein the monoalkyl, dialkyl or aryl moiety may be $R_5$-substituted or unsubstituted, ($R_5$-substituted aryl) oxymethyl, hydroxy-substituted alkanoyloxy, or benzoyloxy wherein $R_5$ is alkyl or alkoxy, $R_3$ is hydrogen, straight or branched chain alkyl of 1–6 carbon atoms, cycloalkylmethyl, or alkylphenyl or a pharmaceutically acceptable salt thereof with the proviso that the compound is not chlidanthine, leucotamine or sanguinine.

38. A compound of the formula

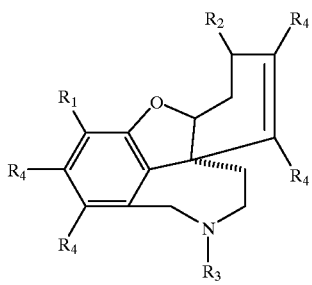

wherein $R_1$ is selected from the group consisting of hydrogen, hydroxy, amino, alkylamino, cyano, sulfhydryl, alkoxy of from 1 to 6 carbon atoms, aryloxy, aralkoxy, $R_5$-substituted aryloxy, a monoalkyl, dialkyl or aryl carbamate group, wherein the monoalkyl, dialkyl or aryl moiety may be $R_5$-substituted or unsubstituted, ($R_5$-substituted aryl) oxymethyl, hydroxy-substituted alkanoyloxy, or benzoyloxy, wherein $R_5$ is alkyl or alkoxy;

$R_2$ is selected from the group consisting of hydrogen, amino, alkylamino, cyano, sulfhydryl, alkoxy of from 1 to 6 carbon atoms, aryloxy, aralkoxy, $R_5$-substituted aryloxy, a monoalkyl, dialkyl or aryl carbamate group, wherein the monoalkyl, dialkyl or aryl moiety may be $R_5$-substituted or unsubstituted, ($R_5$-substituted aryl) oxymethyl, hydroxy-substituted alkanoyloxy, or benzoyloxy, wherein $R_5$ is alkyl or alkoxy;

$R_3$ is hydrogen, straight or branched chain alkyl of 1–6 carbon atoms, cycloalkylmethyl, or alkylphenyl;

each $R_4$ is independently selected from the group consisting of hydrogen, hydroxyl, sulfhydryl, alkyl, aryl, alkoxy, aryloxy, alkaryloxy, nitro, amino, N-alkylamino, N-alkarylamino, fluoro, chloro, bromo, iodo, and trifluoromethyl or a pharmaceutically acceptable salt thereof with the proviso that the compound is not leucotamine, O-methylleucotamine, O-methylleucotamine acetate, chlidanthine, habranthine or N,O-diacetyl-N-desmethylgalanthamine.

39. A compound of the formula

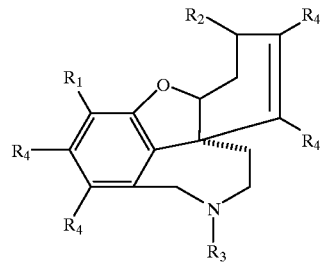

wherein $R_1$ is hydroxy, alkoxy of 1–6 carbon atoms or alkanoyloxy of 1–6 carbon atoms, $R_2$ is OCONHR wherein R is alkyl of 1–6 carbon atoms, phenyl, $R_5$-substituted phenyl, or $R_5$-substituted benzyl wherein $R_5$ is selected from alkyl or alkoxy; $R_3$ is hydrogen, lower alkyl or cyclopropylmethyl and each of $R_4$ is hydrogen or a pharmaceutically acceptable salt thereof.

40. A compound of the formula

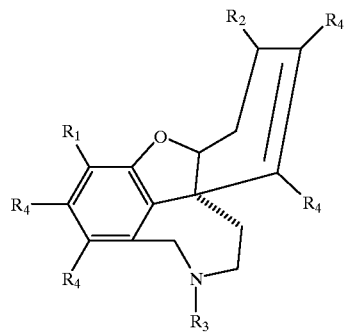

wherein $R_1$ is selected from the group consisting of hydrogen, hydroxy, amino, alkylamino, cyano, sulfhydryl, aryloxy, aralkoxy, a monoalkyl, dialkyl or aryl carbamate group, wherein the monoalkyl, dialkyl or aryl moiety may be $R_5$-substituted or unsubstituted, ($R_5$-substituted aryl)oxymethyl, hydroxy-substituted alkanoyloxy, or benzoyloxy, wherein $R_5$ is alkyl or alkoxy;

$R_2$ is selected from the group consisting of hydrogen, hydroxy, amino, alkylamino, cyano, sulfhydryl, alkoxy of from 1 to 6 carbon atoms, aryloxy, aralkoxy, $R_5$-substituted aryloxy, a monoalkyl, dialkyl or aryl carbamate group, wherein the monoalkyl, dialkyl or aryl moiety may be $R_5$-substituted or unsubstituted, ($R_5$-substituted aryl)oxmethyl, alkanoyloxy, hydroxy-substituted alkanoyloxy, or benzoyloxy, wherein $R_5$ is alkyl or alkoxy;

$R_3$ is hydrogen, straight or branched chain alkyl of 1–6 carbon atoms, cycloalkylmethyl, or alkylphenyl;

each $R_4$ is independently selected from the group consisting of hydrogen, hydroxyl, alkyl, alkoxy, fluoro, chloro, bromo, iodo and trifluoromethyl or a pharmaceutically acceptable salt thereof with the proviso that the compound is not leucotamine, sanguinine, or chlidanthine.

41. A method of inhibiting acetylcholinesterase activity in a patient which comprises administering to the patient a therapeutically effective amount of a compound of the formula

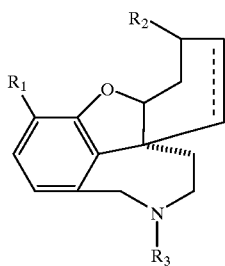

wherein the broken line represents an optionally present double bond and wherein $R_1$ and $R_2$ are each selected from the group consisting of hydrogen, sulfhydryl, amino, alkylamino, OR,

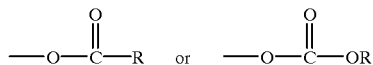

wherein R is alkyl of from 1–6 carbon atoms, phenyl, benzyl, $R_5$-substituted phenyl, or $R_5$-substituted benzyl wherein $R_5$ is selected from the group consisting of hydroxyl, sulfhydryl, alkyl, aryl, alkoxy, aryloxy, nitro, amino, N-alkylamino, N-arylamino, fluoro, chloro, bromo, iodo and trifluoromethyl, $R_3$ is selected from hydrogen, branched or linear alkyl of 1 to 6 carbon atoms,

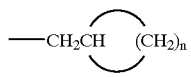

wherein n is 3, 4, or 5, or

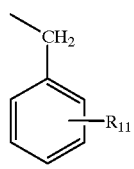

wherein $R_{11}$ is hydrogen, alkyl or alkoxy; or a pharmaceutically acceptable salt thereof.

42. A compound of the formula

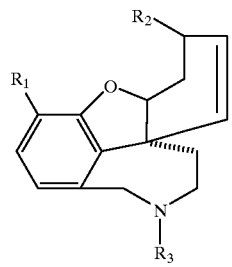

wherein $R_1$ and $R_2$ are each selected from the group consisting of hydrogen, sulfhydryl, amino, alkylamino, OR,

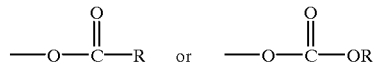

wherein R is alkyl of from 1–6 carbon atoms, phenyl, benzyl, $R_5$-substituted phenyl or $R_5$-substituted benzyl wherein $R_5$ is selected from the group consisting of hydroxyl, sulfhydryl, alkyl, aryl, alkoxy, aryloxy, nitro, amino, N-alkylamino, N-arylamino, fluoro, chloro, bromo, iodo and trifluoromethyl, $R_3$ selected from hydrogen, branched or linear alkyl of 1 to 6 atoms,

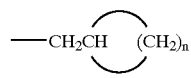

wherein n is 3, 4, or 5, or

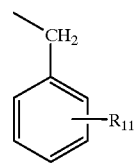

wherein $R_{11}$ is hydrogen, alkyl or alkoxy; or a pharmaceutically acceptable salt thereof.

43. A compound of the formula

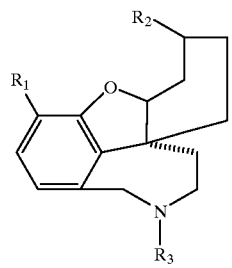

wherein $R_1$ and $R_2$ are each selected from the group consisting of hydrogen, sulfhydryl, amino, alkylamino, OR,

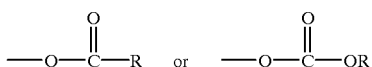

wherein R is alkyl of from 1–6 carbon atoms, phenyl, benzyl, $R_5$-substituted phenyl, or $R_5$-substituted benzyl wherein $R_5$ is selected from the group consisting of hydroxyl, sulfhydryl, alkyl, aryl, alkoxy, aryloxy, nitro, amino, N-alkylamino, N-arylamino, fluoro, chloro, bromo, iodo and trifluoromethyl;

$R_3$ is selected from hydrogen, straight or branched alkyl of 1 to 6 carbon atoms,

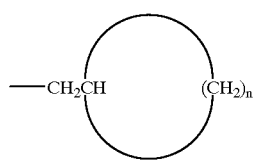

wherein n is 3, 4, or 5 or

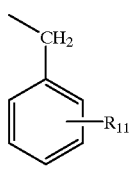

wherein $R_{11}$ is hydrogen, alkyl or alkoxy; or a pharmaceutically acceptable salt thereof.

44. A pharmaceutical composition comprising a compound of the formula

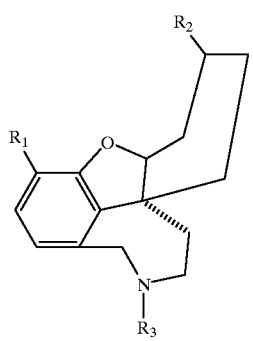

wherein $R_1$ is selected from the group consisting of hydrogen, amino, alkylamino, cyano, sulfhydryl, aryloxy, aralkoxy, $R_5$-substituted aryloxy, a monoalkyl, dialkyl or aryl carbamate group, wherein the monoalkyl, dialkyl or aryl group is $R_5$-substituted or unsubstituted, ($R_5$-substituted aryl)oxymethyl, hydroxy-substituted alkanoyloxy, benzoyloxy, $R_5$-substituted benzoyloxy, wherein $R_5$ is alkyl or alkoxy;

$R_2$ is selected from the group consisting of hydrogen, hydroxy, amino, alkylamino, cyano, sulfhydryl, alkoxy of from 1 to 6 carbon atoms, aryloxy, aralkoxy, $R_5$-substituted aryloxy, a monoalkyl, dialkyl or aryl carbamate group, ($R_5$-substituted aryl)oxymethyl, alkanoyloxy, hydroxy-substituted alkanoyloxy, or benzoyloxy, wherein $R_5$ is alkyl or alkoxy;

$R_3$ is hydrogen, straight or branched chain alkyl of 1–6 carbon atoms, -cycloalkylmethyl or alkylphenyl; or a pharmaceutically acceptable salt and a pharmaceutically acceptable diluent, solvent or carrier with the proviso that the compound is not chlidanthine, or leucotamine.

45. A compound of the formula:

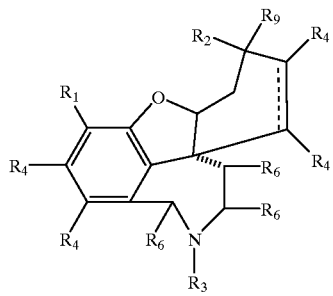

wherein the broken line represents an optionally present double bond;

$R_1$ and $R_2$ are each selected independently from the group consisting of hydrogen, hydroxy, amino, alkylamino, cyano, sulfhydryl, alkoxy of 1–6 carbon atoms, aryloxy, aralkoxy, $C_{1-6}$ alkyl carbonate, $R_5$-substituted phenyl carbonate, $R_5$-substituted benzyl carbonate, $R_5$-substituted aryloxy, monoalkyl, dialkyl or aryl carbamate group, wherein the monoalkyl, dialkyl or aryl moiety be $R_5$-substituted or unsubstituted, ($R_5$-substituted aryl)oxmethyl, alkanoyloxy, hydroxy-substituted alkanoyloxy, or benzoyloxy;

$R_1$ may also be alkyl of up to 14 carbon atoms or hydroxymethyl; $R_2$ may also be carboxymethyl provided that at least one of $R_1$ and $R_2$ is hydroxy; amino or alkylamino; $R_3$ is a residue of a compound having adrenergic or monoamine oxidase activity and said residue is selected from the group consisting of a)

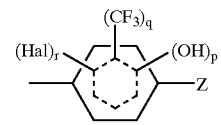

wherein Hal is halogen, p is 0, 1 or 2, q is 0 or 1, r is 0 or 1 and Z is selected from the group consisting of i)

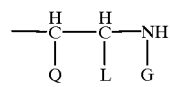

wherein Q is hydrogen or hydroxy, L is hydrogen or $C_{1-4}$ alkyl, G is hydrogen, $C_{1-4}$ alkyl, or alkylphenyl wherein said phenyl group is optionally substituted by hydroxy or methylene dioxy, or is alkylamino;

ii) 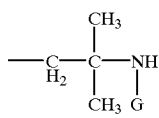

wherein G is as defined above, iii) 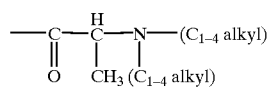

iv) 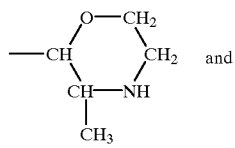

v) 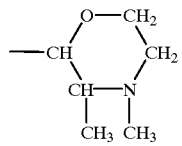

b) 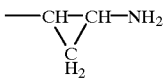

c) 

d) 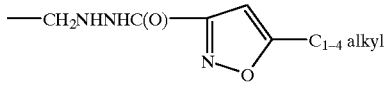

each $R_4$ group is independently selected from hydrogen, hydroxy, alkyl, alkoxy, fluoro, chloro, bromo, iodo, and trifluoromethyl; $R_5$ is selected from the group consisting of hydroxyl, sulfhydryl, alkyl, aryl, alkoxy, aryloxy, alkaryloxy, nitro, amino, N-alkylamino, N-arylamino, fluoro, chloro, bromo, iodo and trifluoromethyl;

$R_6$ is hydrogen, halo, trifluoromethyl or alkyl of 1 to 4 carbon atoms; $R_9$ is hydrogen or alkyl of 1 to 6 carbon atoms or a pharmaceutically acceptable acid addition salt thereof.

46. A pharmaceutical composition comprising a compound of the formula:

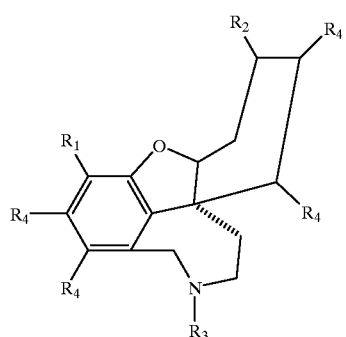

wherein $R_1$ is selected from the group consisting of hydrogen, amino, alkylamino, cyano, sulfhydryl, aryloxy, aralkoxy, $R_5$-substituted aryloxy, a monoalkyl, dialkyl or aryl carbamate group wherein the monoalkyl, dialkyl or aryl moiety may be $R_5$-substituted or unsubstituted, ($R_5$-substituted aryl)oxymethyl, hydroxy-substituted alkanoyloxy, or benzoyloxy, wherein $R_5$ is alkyl or alkoxy;

$R_2$ is selected from the group consisting of hydrogen, hydroxy, amino, alkylamino, cyano, sulfhydryl, alkoxy of from 1 to 6 carbon atoms, aryloxy, aralkoxy, $R_5$-substituted aryloxy, a monoalkyl, dialkyl or aryl carbamate group, wherein the monoalkyl, dialkyl or aryl moiety may be $R_5$-substituted or unsubstituted, ($R_5$-substituted aryl)oxymethyl, alkanoyloxy, hydroxy-substituted alkanoyloxy, or benzoyloxy, wherein $R_5$ is alkyl or alkoxy;

$R_3$ is hydrogen, straight or branched chain alkyl of 1–6 carbon atoms, cycloalkylmethyl or alkylphenyl;

each $R_4$ is independently selected from the group consisting of hydrogen, hydroxyl, alkyl, alkoxy, fluoro, chloro, bromo, iodo and trifluoromethyl provided that $R_2$ is not hydroxy or methoxy when $R_1$ is hydrogen and $R_3$ is methyl and $R_4$ is hydrogen, or a pharmaceutically acceptable salt thereof and a pharmaceutically acceptable diluent, solvent or carrier.

47. A pharmaceutical composition comprising a compound of the formula:

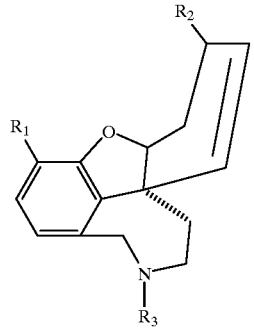

wherein $R_1$ is selected from the group consisting of hydrogen, hydroxy, amino, alkylamino, cyano, sulfhydryl, alkoxy of from 1 to 6 carbon atoms, aryloxy, aralkoxy, $R_5$-substituted aryloxy, a monoalkyl, dialkyl or aryl carbamate group, wherein the monoalkyl, dialkyl or aryl moiety may be $R_5$-substituted or unsubstituted, ($R_5$-substituted aryl) oxmethyl, alkanoyloxy, hydroxy-substituted alkanoyloxy, benzoyloxy or aryloxycarboxyl, wherein $R_5$ is alkyl or alkoxy;

$R_2$ is selected from the group consisting of hydrogen, amino, alkylamino, cyano, sulfhydryl, alkoxy of 1 to 6 carbon atoms, aryloxy, aralkoxy, $R_5$-substituted aryloxy, a monoalkyl, dialkyl or aryl carbamate, wherein the monoalkyl dialkyl or aryl moiety may be $R_5$-substituted or unsubstituted, ($R_5$-substituted aryl) oxmethyl, alkanoyloxy, hydroxy-substituted alkanoyloxy, or benzoyloxy wherein $R_5$ is alkyl or alkoxy;

$R_3$ is hydrogen, straight or branched chain alkyl of 1–6 carbon atoms, cycloalkylmethyl, or alkylphenyl or a pharmaceutically acceptable salt thereof and a pharmaceutically acceptable diluent, solvent or carrier with the proviso that the compound is not chlidanthine, leucotamine or sanguinine.

48. A pharmaceutical composition comprising a compound of the formula:

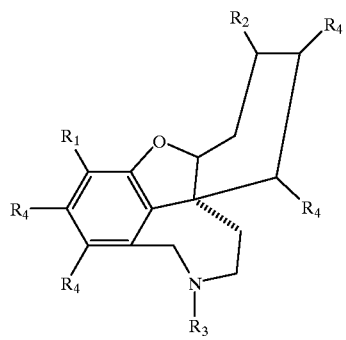

wherein $R_1$ is selected from the group consisting of hydrogen, hydroxy, amino, alkylamino, cyano, sulfhydryl, aryloxy, aralkoxy, $R_5$-substituted aryloxy, a monoalkyl, dialkyl or aryl carbamate group, wherein the monoalkyl, dialkyl or aryl moiety may be $R_5$-substituted or unsubstituted, ($R_5$-substituted aryl) oxmethyl, alkanoyloxy, hydroxy-substituted alkanoyloxy, or benzoyloxy, wherein $R_5$ is alkyl or alkoxy;

$R_2$ is selected from the group consisting of hydrogen, hydroxy, amino, alkylamino, cyano, sulfhydryl, alkoxy of from 1 to 6 carbon atoms, aryloxy, aralkoxy, $R_5$-substituted aryloxy, a monoalkyl, dialkyl or aryl carbamate group, wherein the monoalkyl, dialkyl or aryl moiety may be $R_5$-substituted or unsubstituted, ($R_5$-substituted aryl)oxymethyl, alkanoyloxy, hydroxy-substituted alkanoyloxy, or benzoyloxy, wherein $R_5$ is alkyl or alkoxy;

$R_3$ is hydrogen, straight or branched chain alkyl of 1–6 carbon atoms, cycloalkylmethyl or alkylphenyl; each $R_4$ is independently selected from the group consisting of hydrogen, hydroxyl, alkyl, alkoxy, fluoro, chloro, bromo, iodo and trifluoromethyl or a pharmaceutically acceptable salt thereof and a pharmaceutically acceptable diluent, solvent or carrier with the proviso that the compound is not leucotamine, sanguine or chlidanthine.

49. A method as claimed in claim 1 wherein the compound is one wherein $R_1$ is alkoxy of 1–6 carbon atoms.

50. A compound as claimed in claim 37 wherein $R_1$ is alkoxy of 1–6 carbon atoms.

51. A compound as claimed in claim 38 wherein $R_1$ is alkoxy of 1–6 carbon atoms.

52. A method of as claimed in claim 41 wherein the compound is one wherein $R_1$ is alkoxy of 1–6 carbon atoms.

53. A compound as claimed in claim 42 wherein $R_1$ is alkoxy of 1–6 carbon atoms.

54. A compound as claimed in claim 43 wherein $R_1$ is alkoxy of 1–6 carbon atoms.

55. A pharmaceutical composition comprising a compound of the formula:

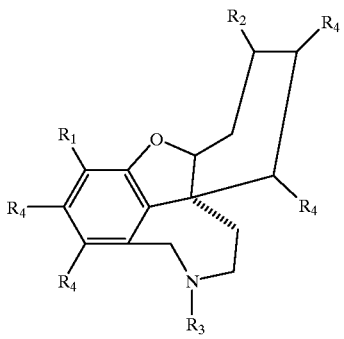

wherein $R_1$ is selected from the group consisting of hydrogen, amino, alkylamino, cyano, sulfhydryl, alkoxy of 1 to 6 carbon atoms, aryloxy, aralkoxy, $R_5$-substituted aryloxy, a monoalkyl, dialkyl or aryl carbamate group, wherein the monoalkyl, dialkyl or aryl group may be $R_5$-substituted or unsubstituted, ($R_5$-substituted aryl)oxymethyl, hydroxy-substituted alkanoyloxy, or benzoyloxy, wherein $R_5$ is alkyl or alkoxy;

$R_2$ is selected from the group consisting of hydrogen, hydroxy, amino, alkylamino, cyano, sulfhydryl, alkoxy of from 1 to 6 carbon atoms, aryloxy, aralkoxy, $R_5$-substituted aryloxy, a monoalkyl, dialkyl or aryl carbamate group wherein the monoalkyl, dialkyl or aryl group may be $R_5$-substituted or unsubstituted, ($R_5$-substituted aryl)oxymethyl, alkanoyloxy, hydroxy-substituted alkanoyloxy, benzoyloxy, or $R_5$-substituted benzoyloxy, wherein $R_5$ is alkyl or alkoxy;

$R_3$ is hydrogen, straight or branched chain alkyl of 1–6 carbon atoms, cycloalkylmethyl or alkylphenyl;

each $R_4$ is independently selected from the group consisting of hydrogen, hydroxy, alkyl, alkoxy, fluoro, chloro, bromo, iodo and trifluoromethyl provided that $R_2$ is not hydroxy or methoxy when $R_1$ is hydrogen and $R_3$ is methyl and $R_4$ is hydrogen, and a pharmaceutically acceptable diluent, solvent or carrier.

56. A composition according to claim 55 wherein $R_2$ is selected from the group consisting of hydrogen, amino, alkylamino, cyano, sulfhydryl, alkoxy of from 1 to 6 carbon atoms, aryloxy, aralkoxy, $R_5$-substituted aryloxy, a monoalkyl, dialkyl or aryl carbamate group, ($R_5$-substituted aryl)oxymethyl, alkanoyloxy, or hydroxy-substituted alkanoyloxy, benzoyloxy, wherein $R_5$ is alkyl or alkoxy.

57. A pharmaceutical composition as claimed in claim 47 wherein the compound is one wherein $R_1$ is alkoxy of 1–6 carbon atoms.

58. A pharmaceutical composition comprising a compound of the formula

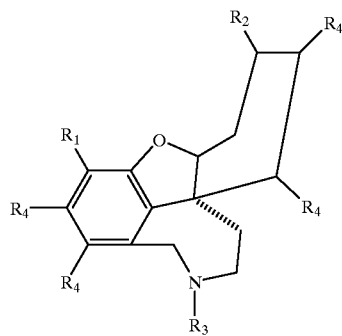

wherein $R_1$ is selected from the group consisting of hydrogen, hydroxy, amino, alkylamino, cyano, sulfhydryl, aryloxy, alkoxy of 1 to 6 carbon atoms, aralkoxy, $R_5$-substituted aryloxy, a monoalkyl, dialkyl or aryl carbamate group, wherein the monoalkyl, dialkyl or aryl group may be $R_5$-substituted or unsubstituted, ($R_5$-substituted aryl)oxymethyl, alkanoyloxy, hydroxy-substituted alkanoyloxy, or benzoyloxy, wherein $R_5$ is alkyl or alkoxy;

$R_2$ is selected from the group consisting of hydrogen, hydroxy, amino, alkylamino, cyano, sulfhydryl, alkoxy of from 1 to 6 carbon atoms, aryloxy, aralkoxy, $R_5$-substituted aryloxy, a monoalkyl, dialkyl or aryl carbamate group wherein the monoalkyl, dialkyl or aryl moiety may be $R_5$-substituted or unsubstituted, ($R_5$-substituted aryl)oxymethyl, alkanoyloxy, hydroxy-substituted alkanoyloxy, or benzoyloxy, wherein $R_5$ is alkyl or alkoxy;

$R_3$ is hydrogen, straight or branched chain alkyl of 1–6 carbon atoms, cycloalkylmethyl or alkylphenyl;

each $R_4$ is independently selected from the group consisting of hydrogen, hydroxyl, alkyl, alkoxy, fluoro, chloro, bromo, iodo and trifluoromethyl or a pharmaceutically acceptable salt thereof with the proviso that the compound is not leucotamine, chlidanthine and $R_1$ is not alkoxy of 1–6 carbon atoms when $R_2$ is hydroxy, $R_3$ is methyl and all $R_4$'s are hydrogen.

59. A pharmaceutical composition according to claim 58 wherein $R_2$ is selected from the group consisting of hydrogen, amino, alkylamino, cyano, sulfhydryl, alkoxy of from 1 to 6 carbon atoms, aryloxy, aralkoxy, $R_5$-substituted aryloxy, a monoalkyl, aryl or benzyl carbamate group, ($R_5$-substituted aryl)oxymethyl, alkanoyloxy, hydroxy-substituted alkanoyloxy, or benzyloxy, wherein $R_5$ is alkyl or alkoxy.

60. A method according to claim 4 wherein said compound is one wherein $R_3$ and $R_4$ are all hydrogen and $R_1$ is alkoxy of 1 to 6 carbon atoms.

61. A compound as claimed in claim 43 wherein $R_1$ is a carbonate group.

62. A compound as claimed in claim 37 wherein $R_1$ is alkanoyloxy or a monoalkyl, dialkyl or aryl carbamate, wherein the aryl group may be $R_5$-substituted.

63. A pharmaceutical composition as claimed in claim 22 wherein the compound is one wherein $R_1$ is alkanoyloxy or a monoalkyl, dialkyl or aryl carbamate wherein the aryl group may be $R_5$-substituted.

64. A compound as claimed in claim 42 wherein $R_1$ is a carbonate group.

65. A pharmaceutical composition as claimed in claim 47 wherein the compound is one wherein $R_1$ is alkanoyloxy or a monoalkyl, dialkyl or aryl carbamate, wherein the aryl group may be $R_5$-substituted.

66. A pharmaceutical composition as claimed in claim 48 wherein the active compound is one wherein $R_1$ is alkanoyloxy or a monoalkyl, dialkyl or aryl carbamate, wherein the aryl group may be $R_5$-substituted.

67. A method of inhibiting acetylcholinesterase activity as claimed in claim 41 wherein the compound used is one wherein $R_1$ is a carbonate group.

* * * * *